(12) United States Patent
Navis et al.

(10) Patent No.: US 11,035,860 B2
(45) Date of Patent: Jun. 15, 2021

(54) AUTO-ACTIVE AND INTRACELLULAR MUTANT OF MET

(71) Applicants: Stichting Katholieke Universiteit, Nijmegen (NL); Stichting VU-Vumc, Amsterdam (NL)

(72) Inventors: Anna Catharina Navis, Järfälla (SE); Wilhelmus Petrus Johannes Leenders, Nijmegen (NL); Thomas Würdinger, Amsterdam (NL)

(73) Assignees: Stichting Katholieke Universiteit; Stichting Vu-Vumuc

( * ) Notice: Subject to any disclaimer, the term of this patent is extended or adjusted under 35 U.S.C. 154(b) by 27 days.

(21) Appl. No.: 15/528,322

(22) PCT Filed: Nov. 18, 2015

(86) PCT No.: PCT/EP2015/076989
§ 371 (c)(1),
(2) Date: May 19, 2017

(87) PCT Pub. No.: WO2016/079194
PCT Pub. Date: May 26, 2016

(65) Prior Publication Data
US 2017/0322215 A1   Nov. 9, 2017

(30) Foreign Application Priority Data

Nov. 20, 2014   (EP) .................................... 14194066

(51) Int. Cl.
| | |
|---|---|
| *C12Q 1/68* | (2018.01) |
| *G01N 33/574* | (2006.01) |
| *C12Q 1/6886* | (2018.01) |
| *C07K 14/71* | (2006.01) |
| *C12Q 1/6883* | (2018.01) |
| *G01N 33/74* | (2006.01) |
| *A61K 39/00* | (2006.01) |
| *C07K 16/28* | (2006.01) |

(52) U.S. Cl.
CPC ......... *G01N 33/5748* (2013.01); *C07K 14/71* (2013.01); *C12Q 1/6883* (2013.01); *C12Q 1/6886* (2013.01); *G01N 33/574* (2013.01); *G01N 33/74* (2013.01); *A61K 2039/505* (2013.01); *C07K 16/2863* (2013.01); *C12Q 2600/106* (2013.01); *C12Q 2600/156* (2013.01); *G01N 2333/71* (2013.01)

(58) Field of Classification Search
None
See application file for complete search history.

(56) References Cited

FOREIGN PATENT DOCUMENTS

| EP | 2119448 A1 | 11/2009 |
|---|---|---|
| WO | 2008/113013 A2 | 9/2008 |
| WO | 2013/079973 A1 | 6/2013 |

OTHER PUBLICATIONS

Ma et al. Cancer Research 63, 6272-6281, Oct. 1, 2003 (Year: 2003).*
Kongkai Zhu, Xiangqian Kong, Dan Zhao, Zhongjie Liang & Cheng Luo (2014) c-MET kinase inhibitors: a patent review (2011-2013), Expert Opinion on Therapeutic Patents, 24:2, 217-230, DOI: 10.1517/13543776.2014.864279 (Year: 2014).*
Mo and Liu Chronic Diseases and Translational Medicine 3 (2017) 148-153 (Year: 2017).*
Garber. Nature Reviews. vol. 13 Aug. 2014, pp. 563-565 (Year: 2014).*
Pollack. Am Fam Physician 2007;75:231-6, 239-40. Copyright © 2007 American Academy of Family Physicians (Year: 2007).*
Kong-Beltran, Monica, et al., Somatic Mutations Lead to an Oncogenic Deletion of Met in Lung Cancer, American Association for Cancer Research Journal, vol. 66, No. 1, Jan. 1, 2006, pp. 283-289 (plus supplementary figures and figure legends) (18 pages).
Lin, Jenny C. et al., Intron-exon structure of the MET gene and cloning of an alternatively-spliced Met isoform reveals frequent exon-skipping of a single large internal exon, Oncogene, Nature Publishing Group, GB, vol. 16, No. 7, Feb. 19, 1998, pp. 833-842 (10 pages).
International Search Report, Intl. Appl. No. PCT/EP2015/076989, dated Feb. 5, 2016 (7 pages).
Shukla et al., hg19KIndel: ethnicity normalized human reference genome, BMC Genomics (2019) 20:459.

* cited by examiner

*Primary Examiner* — Juliet C Switzer
(74) *Attorney, Agent, or Firm* — McDonnell Boehnen Hulbert & Berghoff LLP

(57) ABSTRACT

The present invention relates to the fields of medicine and molecular diagnostics. In particular, it relates to a novel method for the treatment, prevention and/or delay of cancer and to a diagnostic method involving detection of a novel auto-active and intracellular mutant of MET.

4 Claims, 11 Drawing Sheets

Figure 1A:
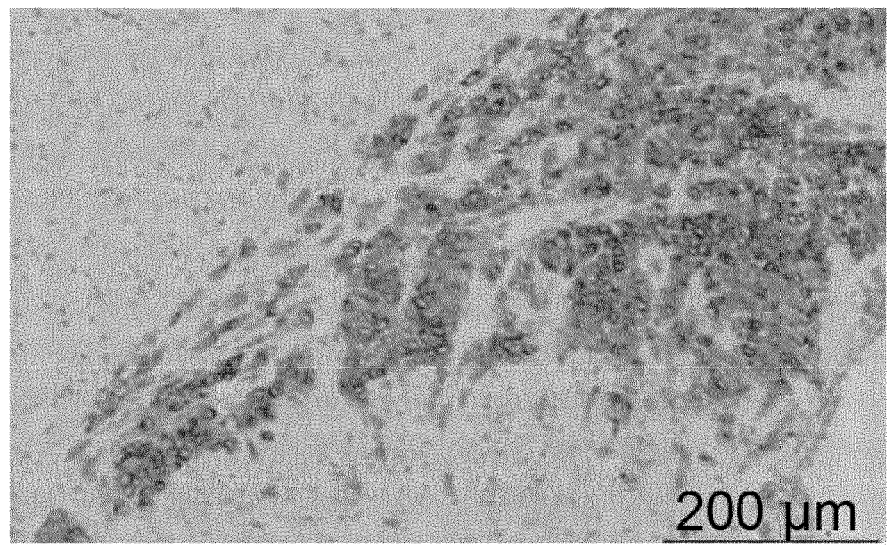

Specification includes a Sequence Listing.

SEQUENCE LISTING

<160> NUMBER OF SEQ ID NOS: 23

<210> SEQ ID NO 1
<211> LENGTH: 20
<212> TYPE: DNA
<213> ORGANISM: Artificial
<220> FEATURE:
<223> OTHER INFORMATION: PCR primer HGF-Fw204

<400> SEQUENCE: 1
ctgcagcatg tcctcctgca                                          20

<210> SEQ ID NO 2
<211> LENGTH: 20
<212> TYPE: DNA
<213> ORGANISM: Artificial
<220> FEATURE:
<223> OTHER INFORMATION: PCR primer HGF-Rv504

<400> SEQUENCE: 2
gaggtcaaat tcatggccaa                                          20

<210> SEQ ID NO 3
<211> LENGTH: 20
<212> TYPE: DNA
<213> ORGANISM: Artificial
<220> FEATURE:
<223> OTHER INFORMATION: PCR primer p361-Fw

<400> SEQUENCE: 3
tgccagagaa gagtgtggtg                                          20

<210> SEQ ID NO 4
<211> LENGTH: 21
<212> TYPE: DNA
<213> ORGANISM: Artificial
<220> FEATURE:
<223> OTHER INFORMATION: PCR primer p425-Rv

<400> SEQUENCE: 4
gttaagctgc cgtgcaacat c                                        21

<210> SEQ ID NO 5
<211> LENGTH: 20
<212> TYPE: DNA
<213> ORGANISM: Artificial
<220> FEATURE:
<223> OTHER INFORMATION: PCR primer MET 1997-Fw

<400> SEQUENCE: 5
ctccttggaa atgagagctg                                          20

<210> SEQ ID NO 6
<211> LENGTH: 21
<212> TYPE: DNA
<213> ORGANISM: Artificial
<220> FEATURE:
<223> OTHER INFORMATION: PCR primer MET2342Rv

<400> SEQUENCE: 6
cagttgaaat ggtttgggct g                                        21

<210> SEQ ID NO 7
<211> LENGTH: 20
<212> TYPE: DNA
<213> ORGANISM: Artificial

```
<220> FEATURE:
<223> OTHER INFORMATION: PCR primer MET1997Fw

<400> SEQUENCE: 7
ctccttggaa atgagagctg                                               20

<210> SEQ ID NO 8
<211> LENGTH: 19
<212> TYPE: DNA
<213> ORGANISM: Artificial
<220> FEATURE:
<223> OTHER INFORMATION: PCR primer MET2414Rev

<400> SEQUENCE: 8
gggatcttca cggtaactg                                                19

<210> SEQ ID NO 9
<211> LENGTH: 29
<212> TYPE: DNA
<213> ORGANISM: Artificial
<220> FEATURE:
<223> OTHER INFORMATION: PCR primer MET173EcoR1-Fw

<400> SEQUENCE: 9
cgaattcgat aaacctctca taatgaagg                                     29

<210> SEQ ID NO 10
<211> LENGTH: 29
<212> TYPE: DNA
<213> ORGANISM: Artificial
<220> FEATURE:
<223> OTHER INFORMATION: PCR primer MET4421NotI-Rv

<400> SEQUENCE: 10
agcggccgcc tatgatgtct cccagaagg                                     29

<210> SEQ ID NO 11
<211> LENGTH: 23
<212> TYPE: DNA
<213> ORGANISM: Artificial
<220> FEATURE:
<223> OTHER INFORMATION: PCR primer MET173Fw

<400> SEQUENCE: 11
gataaacctc tcataatgaa ggc                                           23

<210> SEQ ID NO 12
<211> LENGTH: 28
<212> TYPE: DNA
<213> ORGANISM: Artificial
<220> FEATURE:
<223> OTHER INFORMATION: PCR primer MET3028NheI-Rv

<400> SEQUENCE: 12
cgctagcctg atctggttga actattac                                      28

<210> SEQ ID NO 13
<211> LENGTH: 1390
<212> TYPE: PRT
<213> ORGANISM: Homo sapiens

<400> SEQUENCE: 13

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
```

```
                    20                  25                  30
Ser Glu Met Asn Val Asn Met Lys Tyr Gln Leu Pro Asn Phe Thr Ala
                35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
                115                 120                 125

Gln Leu Ile Ser Cys Gly Ser Val Asn Arg Gly Thr Cys Gln Arg His
                130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
                210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445
```

```
Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860
```

```
Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
        900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
        930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln
        1010                1015                1020

Val Gln Tyr Pro Leu Thr Asp Met Ser Pro Ile Leu Thr Ser Gly
        1025                1030                1035

Asp Ser Asp Ile Ser Ser Pro Leu Leu Gln Asn Thr Val His Ile
        1040                1045                1050

Asp Leu Ser Ala Leu Asn Pro Glu Leu Val Gln Ala Val Gln His
        1055                1060                1065

Val Val Ile Gly Pro Ser Ser Leu Ile Val His Phe Asn Glu Val
        1070                1075                1080

Ile Gly Arg Gly His Phe Gly Cys Val Tyr His Gly Thr Leu Leu
        1085                1090                1095

Asp Asn Asp Gly Lys Lys Ile His Cys Ala Val Lys Ser Leu Asn
        1100                1105                1110

Arg Ile Thr Asp Ile Gly Glu Val Ser Gln Phe Leu Thr Glu Gly
        1115                1120                1125

Ile Ile Met Lys Asp Phe Ser His Pro Asn Val Leu Ser Leu Leu
        1130                1135                1140

Gly Ile Cys Leu Arg Ser Glu Gly Ser Pro Leu Val Val Leu Pro
        1145                1150                1155

Tyr Met Lys His Gly Asp Leu Arg Asn Phe Ile Arg Asn Glu Thr
        1160                1165                1170

His Asn Pro Thr Val Lys Asp Leu Ile Gly Phe Gly Leu Gln Val
        1175                1180                1185

Ala Lys Gly Met Lys Tyr Leu Ala Ser Lys Lys Phe Val His Arg
        1190                1195                1200

Asp Leu Ala Ala Arg Asn Cys Met Leu Asp Glu Lys Phe Thr Val
        1205                1210                1215

Lys Val Ala Asp Phe Gly Leu Ala Arg Asp Met Tyr Asp Lys Glu
        1220                1225                1230

Tyr Tyr Ser Val His Asn Lys Thr Gly Ala Lys Leu Pro Val Lys
        1235                1240                1245

Trp Met Ala Leu Glu Ser Leu Gln Thr Gln Lys Phe Thr Thr Lys
        1250                1255                1260

Ser Asp Val Trp Ser Phe Gly Val Leu Leu Trp Glu Leu Met Thr
```

```
            1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 14
<211> LENGTH: 1310
<212> TYPE: PRT
<213> ORGANISM: Homo sapiens

<400> SEQUENCE: 14

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240
```

```
Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Val Ser Asn
    610                 615                 620

Ser Ile Leu Glu Cys Tyr Thr Pro Ala Gln Thr Ile Ser Thr Glu Phe
625                 630                 635                 640

Ala Val Lys Leu Lys Ile Asp Leu Ala Asn Arg Glu Thr Ser Ile Phe
                645                 650                 655

Ser Tyr Arg Glu Asp Pro Ile Val Tyr Glu Ile His Pro Thr Lys Ser
```

```
                    660                 665                 670
Phe Ile Ser Gly Gly Ser Thr Ile Thr Gly Val Gly Lys Asn Leu Asn
                675                 680                 685

Ser Val Ser Val Pro Arg Met Val Ile Asn Val His Glu Ala Gly Arg
        690                 695                 700

Asn Phe Thr Val Ala Cys Gln His Arg Ser Asn Ser Glu Ile Ile Cys
705                 710                 715                 720

Cys Thr Thr Pro Ser Leu Gln Gln Leu Asn Leu Gln Leu Pro Leu Lys
                725                 730                 735

Thr Lys Ala Phe Phe Met Leu Asp Gly Ile Leu Ser Lys Tyr Phe Asp
                740                 745                 750

Leu Ile Tyr Val His Asn Pro Val Phe Lys Pro Phe Glu Lys Pro Val
                755                 760                 765

Met Ile Ser Met Gly Asn Glu Asn Val Leu Glu Ile Lys Gly Asn Asp
                770                 775                 780

Ile Asp Pro Glu Ala Val Lys Gly Glu Val Leu Lys Val Gly Asn Lys
785                 790                 795                 800

Ser Cys Glu Asn Ile His Leu His Ser Glu Ala Val Leu Cys Thr Val
                        805                 810                 815

Pro Asn Asp Leu Leu Lys Leu Asn Ser Glu Leu Asn Ile Glu Trp Lys
                820                 825                 830

Gln Ala Ile Ser Ser Thr Val Leu Gly Lys Val Ile Val Gln Pro Asp
                835                 840                 845

Gln Asn Phe Thr Gly Leu Ile Ala Gly Val Val Ser Ile Ser Thr Ala
850                 855                 860

Leu Leu Leu Leu Leu Gly Phe Phe Leu Trp Leu Lys Lys Arg Lys Gln
865                 870                 875                 880

Ile Lys Asp Leu Gly Ser Glu Leu Val Arg Tyr Asp Ala Arg Val His
                        885                 890                 895

Thr Pro His Leu Asp Arg Leu Val Ser Ala Arg Ser Val Ser Pro Thr
                900                 905                 910

Thr Glu Met Val Ser Asn Glu Ser Val Asp Tyr Arg Ala Thr Phe Pro
                915                 920                 925

Glu Asp Gln Phe Pro Asn Ser Ser Gln Asn Gly Ser Cys Arg Gln Val
                930                 935                 940

Gln Tyr Pro Leu Thr Asp Met Ser Pro Ile Leu Thr Ser Gly Asp Ser
945                 950                 955                 960

Asp Ile Ser Ser Pro Leu Leu Gln Asn Thr Val His Ile Asp Leu Ser
                        965                 970                 975

Ala Leu Asn Pro Glu Leu Val Gln Ala Val Gln His Val Val Ile Gly
                980                 985                 990

Pro Ser Ser Leu Ile Val His Phe Asn Glu Val Ile Gly Arg Gly His
                995                 1000                1005

Phe Gly Cys Val Tyr His Gly Thr Leu Leu Asp Asn Asp Gly Lys
                1010                1015                1020

Lys Ile His Cys Ala Val Lys Ser Leu Asn Arg Ile Thr Asp Ile
                1025                1030                1035

Gly Glu Val Ser Gln Phe Leu Thr Glu Gly Ile Ile Met Lys Asp
                1040                1045                1050

Phe Ser His Pro Asn Val Leu Ser Leu Leu Gly Ile Cys Leu Arg
                1055                1060                1065

Ser Glu Gly Ser Pro Leu Val Val Leu Pro Tyr Met Lys His Gly
                1070                1075                1080
```

Asp Leu Arg Asn Phe Ile Arg Asn Glu Thr His Asn Pro Thr Val
    1085                1090                1095

Lys Asp Leu Ile Gly Phe Gly Leu Gln Val Ala Lys Gly Met Lys
    1100                1105                1110

Tyr Leu Ala Ser Lys Lys Phe Val His Arg Asp Leu Ala Ala Arg
    1115                1120                1125

Asn Cys Met Leu Asp Glu Lys Phe Thr Val Lys Val Ala Asp Phe
    1130                1135                1140

Gly Leu Ala Arg Asp Met Tyr Asp Lys Glu Tyr Tyr Ser Val His
    1145                1150                1155

Asn Lys Thr Gly Ala Lys Leu Pro Val Lys Trp Met Ala Leu Glu
    1160                1165                1170

Ser Leu Gln Thr Gln Lys Phe Thr Thr Lys Ser Asp Val Trp Ser
    1175                1180                1185

Phe Gly Val Leu Leu Trp Glu Leu Met Thr Arg Gly Ala Pro Pro
    1190                1195                1200

Tyr Pro Asp Val Asn Thr Phe Asp Ile Thr Val Tyr Leu Leu Gln
    1205                1210                1215

Gly Arg Arg Leu Leu Gln Pro Glu Tyr Cys Pro Asp Pro Leu Tyr
    1220                1225                1230

Glu Val Met Leu Lys Cys Trp His Pro Lys Ala Glu Met Arg Pro
    1235                1240                1245

Ser Phe Ser Glu Leu Val Ser Arg Ile Ser Ala Ile Phe Ser Thr
    1250                1255                1260

Phe Ile Gly Glu His Tyr Val His Val Asn Ala Thr Tyr Val Asn
    1265                1270                1275

Val Lys Cys Val Ala Pro Tyr Pro Ser Leu Leu Ser Ser Glu Asp
    1280                1285                1290

Asn Ala Asp Asp Glu Val Asp Thr Arg Pro Ala Ser Phe Trp Glu
    1295                1300                1305

Thr Ser
    1310

<210> SEQ ID NO 15
<211> LENGTH: 1153
<212> TYPE: DNA
<213> ORGANISM: Homo sapiens

<400> SEQUENCE: 15
gttttcccaa atagtgcacc ccttgaagga gggacaaggc tgaccatatg tggctgggac    60
tttggatttc ggaggaataa taaatttgat ttaaagaaaa ctagagttct ccttggaaat   120
gagagctgca ccttgacttt aagtgagagc acgatgaata cgtaaggatc ttaaaatgct   180
ttstggggtg tgcttggaaa ataggttttg tttttgaatg aatatttctt ttaaaattgc   240
tcaattacct aaacagtggg aattctagac acatttcaat tggtggaaaa acatgtactt   300
taaaaaggtg ttgtaaattt attttttgtt gcatctgtca atttgaatta atatctgtac   360
cttaaaaatt aagcagattg ttttgtgtgt gtgtgtggag aagaaaaatc aagatgttta   420
tttgtttact ctcctactga caaaacttcc tccttccaaa attcatctac tccttttgct   480
gattttctct cctttctctt gttttttagc aatcctactt ttcagttttg tcttcccatc   540
caccctcttt attgttatag cttaggatct tagctatact atgagctgtg agagtctggt   600
cattgataat aatttaaaat aaacattttc atcaagattt gtaattagac taagtcactc   660

```
tggggaagga agaaatgggg aaaattgggt ctggaagaca gttatgtttc tgcttcttag    720
agttggaaga gctcagttta atcaagtacc aaaagtactt taaaggtttt ttttttcaaat  780 ctcaaatgtt ttccagtcaa ggatagcttg tccacaacaa aggtaagttt gagatccagt   840
cagattaaac agcctacact agaaaaggct tccactcagg aaattcccac ttaggaacca   900
ttgagttata tccttttgat tgtggatat aattctaaaa tatgtgtatc tctaatagct    960
aaaattcact tccttaattt tttttgttca gtgtgtcaaa cagtattctt gaatgttata  1020
ccccagccca aaccatttca actgagtttg ctgttaaatt gaaaattgac ttagccaacc  1080
gagagacaag catcttcagt taccgtgaag atcccattgt ctatgaaatt catccaacca  1140
aatcttttat tag                                                    1153

<210> SEQ ID NO 16
<211> LENGTH: 161
<212> TYPE: DNA
<213> ORGANISM: Homo sapiens

<400> SEQUENCE: 16
gttttcccaa atagtgcacc ccttgaagga gggacaaggc tgaccatatg tggctgggac   60
tttggatttc ggaggaataa taaatttgat ttaaagaaaa ctagagttct ccttggaaat  120
gagagctgca ccttgacttt aagtgagagc acgatgaata c                      161

<210> SEQ ID NO 17
<211> LENGTH: 83
<212> TYPE: DNA
<213> ORGANISM: Homo sapiens

<400> SEQUENCE: 17
gtaaggatct taaatgcttt tstggggtgt gcttggaaaa taggttttgt ttttgaatga   60
atatttcttt taaaattgct caa                                           83

<210> SEQ ID NO 18
<211> LENGTH: 63
<212> TYPE: DNA
<213> ORGANISM: Homo sapiens

<400> SEQUENCE: 18
ttacctaaac agtgggaatt ctagacacat ttcaattggt ggaaaaacat gtactttaaa   60
aag                                                                 63

<210> SEQ ID NO 19
<211> LENGTH: 684
<212> TYPE: DNA
<213> ORGANISM: Homo sapiens

<400> SEQUENCE: 19
gtgttgtaaa tttattttttt gttgcatctg tcaatttgaa ttaatatctg taccttaaaa   60
attaagcaga ttgttttgtg tgtgtgtgtg gagaagaaaa atcaagatgt ttatttgttt  120
actctcctac tgacaaaact tcctccttcc aaaattcatc tactcctttt gctgattttt  180
cttcctttct cttgtttttt agcaatccta cttttcagtt ttgtcttccc atccaccctc  240
tttattgtta tagcttagga tcttagctat actatgagct gtgagagtct ggtcattgat  300
aataatttaa ataaacatt ttcatcaaga tttgtaatta gactaagtca ctctggggaa   360
ggaagaaatg gggaaaattg ggtctggaag acagttatgt ttctgcttct tagagttgga  420
agagctcagt ttaatcaagt accaaaagta ctttaaaggt ttttttttca aatctcaaat  480
```

```
gttttccagt caaggatagc ttgtccacaa caaaggtaag tttgagatcc agtcagatta      540
aacagcctac actagaaaag gcttccactc aggaaattcc cacttaggaa ccattgagtt      600 atatccttt gatttgtgga tataattcta aaatatgtgt atctctaata gctaaaattc       660
acttccttaa ttttttttgt tcag                                             684

<210> SEQ ID NO 20
<211> LENGTH: 162
<212> TYPE: DNA
<213> ORGANISM: Homo sapiens

<400> SEQUENCE: 20
tgtgtcaaac agtattcttg aatgttatac cccagcccaa accatttcaa ctgagtttgc       60
tgttaaattg aaaattgact tagccaaccg agagacaagc atcttcagtt accgtgaaga      120
tcccattgtc tatgaaattc atccaaccaa atcttttatt ag                         162

<210> SEQ ID NO 21
<211> LENGTH: 23
<212> TYPE: DNA
<213> ORGANISM: Artificial Sequence
<220> FEATURE:
<223> OTHER INFORMATION: PCR primer

<400> SEQUENCE: 21
gagagcacga tgaatactgt gtc                                               23

<210> SEQ ID NO 22
<211> LENGTH: 23
<212> TYPE: DNA
<213> ORGANISM: Artificial Sequence
<220> FEATURE:
<223> OTHER INFORMATION: PCR primer

<400> SEQUENCE: 22
gttgacatgc cactgtaaag ttc                                               23

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
agatgcttgt ctctcggttg                                                   20
```

AUTO-ACTIVE AND INTRACELLULAR MUTANT OF MET

CROSS REFERENCE TO RELATED APPLICATIONS

This application is a national stage application under 35 U.S.C. § 371 of International Application No. PCT/EP2015/076989, filed on Nov. 18, 2015. This invention relates to and claims the benefit of priority to European Patent Application No. 14194066.8, filed on Nov. 20, 2014, the disclosures of each of which are explicitly herein incorporated by reference in their entirety.

FIELD OF THE INVENTION

The present invention relates to the fields of medicine and molecular diagnostics. In particular, it relates to a novel method for the treatment, prevention and/or delay of cancer and to a diagnostic method involving detection of a novel auto-active and intracellular mutant of MET.

BACKGROUND OF THE INVENTION

The MET proto-oncogene (chromosome 7q31.2) encodes the tyrosine kinase membrane receptor MET (also called Scatter Factor Receptor or Hepatocyte Growth Factor Receptor), which is essential during development. Signaling from the receptor controls epithelial-to-mesenchymal transition (EMT) of myogenic precursor cells during differentiation into skeletal muscle cells (Bladt et al., 1995), a process that involves migration over long distances in the embryo. In adults, MET is involved in tissue regeneration upon injury (Borowiak et al., 2004; Chmielowiec et al., 2007; Huh et al., 2004).

MET is produced as a glycosylated single chain precursor protein of ~190 kDa which, during transport to the membrane, undergoes furin-mediated cleavage in the trans-Golgi network (Komada et al., 1993). The resulting mature receptor consists of an extracellular 50 kDa α-chain, covalently attached via a disulfide bond to a membrane-spanning 140 kDa β-chain (Chan et al., 1988; Liu et al., 1996; Park et al., 1987). The extracellular segment consists of an N-terminal Sema-domain that is involved in ligand binding, a small cysteine-rich domain, and four IPT (Immunoglobulin-like fold shared by Plexins and Transcription factors) domains, which connect the Sema and cysteine-rich domains with the C-terminal β-subunit (Gherardi et al., 2003).

Upon binding of the ligand Hepatocyte Growth Factor (HGF, Scatter Factor), receptor dimerization occurs followed by trans-phosphorylation in the intracellular tyrosine kinase (TK) domain at tyrosine (Y) residues 1230, 1234 and 1235 (Ferracini et al., 1991; Longati et al., 1994). The TK domain subsequently induces autophosphorylation of Y1349 and Y1356 which act as docking sites for signal transduction molecules including GAB1, GRB2, phospholipase-C and SRC (Ponzetto et al., 1994). Phosphorylated GAB1 interacts with molecules like PI3-K and SHP2 which together induce several downstream signaling pathways. MET signaling is mediated by, among others, the PI3-K/AKT and RAS/MAPK pathways, which induce cell cycle progression, survival, cytoskeletal changes and invasion (Gherardi et al., 2012). In addition to its role downstream of HGF, MET can also be involved in signaling of other transmembrane receptors, including VEGFR2, CD44, and Plexin B1 (Lai et al., 2009; Lu et al., 2012). Upon ligand-induced receptor dimerization, MET is internalized via endocytosis and may be recycled (Joffre et al., 2011). Phosphorylation of Y1003 in the juxtamembrane (JM) domain of the receptor leads to ubiquitination and subsequent proteasomal degradation (Hammond et al., 2001; Jeffers et al., 1997; Peschard et al., 2001). Thus, levels of MET in the cell are tightly regulated.

Aberrant activation of MET signaling is a tumor promoting event in a variety of malignancies and can be induced by several mechanisms including overexpression of its ligand and/or the receptor itself, alternative mRNA splicing and crosstalk with other receptors (Corso and Giordano, 2013). MET amplifications have been found in a number of tumor types including glioblastoma (GBM) (Cancer Genome Atlas Research, 2008; Sottoriva et al., 2013) whereas missense mutations in the Sema, the TK and the JM domain have been reported to affect HGF binding, kinase activation and receptor degradation, respectively (Asaoka et al., 2010; Kong-Beltran et al., 2006; Lee and Yamada, 1994; Ma et al., 2005; Ma et al., 2008; Onozato et al., 2009; Peschard et al., 2001; Petrelli et al., 2002).

The significant role that MET plays in tumor progression and metastasis has made it a prime therapeutic target in oncology. There are currently two classes of MET activation inhibitors available which are in different stages of clinical trial: (1) small molecule MET tyrosine kinase inhibitors and (2) therapeutic antibodies against the extracellular domain of MET and against its ligand HGF. The antibodies have been developed to block the interaction between HGF and MET, thereby preventing MET activation. The tyrosine kinase inhibitors inhibit the activity of the intracellular tyrosine kinase domain of the activated MET, thus blocking MET signaling.

There is however a group of patients who do not respond to anti-MET-antibodies or anti-HGF-antibodies. In the current era of personalized treatment it is of high importance to select on forehand which patients will respond to what therapies.

Accordingly, there is an urgent need for a diagnostic test to assess which subjects are likely not to respond to available antibody therapies but will respond to available tyrosine kinase inhibitors and which subjects may develop resistance against the presently available antibody therapies.

DESCRIPTION OF THE INVENTION

The present inventors have surprisingly found a novel auto-active and intracellular MET mutant. The present inventors have found the mutant MET to be present in 6% of high-grade gliomas and 14% of non small cell lung carcinomas. Characterization of the MET mutant in a glioma cell line revealed that it comprises a deletion of exons 7 and 8. The encoded protein lacks parts of the extracellular IPT-domains 1 and 2, encoded by these exons 7 and 8. As a result of the mutation, the MET mutant is located predominantly in the cytosol where it is constitutively active, independent of the presence of HGF. The auto-active nature of this protein, in combination with a lack of transmembrane localization, renders the MET mutant non-targetable for antibodies. Testing for the presence of the MET mutant is therefore warranted for defining treatment strategy. Accordingly, in a first aspect, the present invention provides for a method for determining the presence of a MET mutant in a sample, wherein the MET mutant is an auto-active and intracellular mutant MET. Such method is herein referred to as a method according to the present invention; such mutant MET is herein referred to as a MET mutant or mutant MET according to the present invention. A mutant MET according to the present invention is defined as a MET protein that is auto-active and is located intracellularly; included in the term mutant MET are an RNA, DNA or cDNA encoding such mutant MET protein. Auto-active is defined as that the mutant MET does not need its ligand HGF to activate its tyrosine kinase domain; said tyrosine kinase domain is constitutively active. Intracellularly is herein to be construed that the mutant MET lacks transmembrane localization and is predominantly located in the cytosol; preferably at least 50%, 60%, 70%, 80%, 90%, 95%, 96%, 97%, 98%, 99% or most preferably 100% of the MET protein is located in the cytosol. Within the context of the present invention, the term MET mutant includes all genetic, epigenetic, post-transcriptional and post-translational forms, including variants such as, but not limited to, methylated and phosphorylated variants. Within the context of the present invention, the term "presence of a mutant MET" means a mutant MET is detected, preferably at least 0.1%, 0.2%. 0.3%. 0.4%, 0.5%, 0.6%, 0.7%, 0.8%, 0.9%, 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the MET detected is mutant MET.

A method according to the present invention may be any molecular diagnostic method known to the person skilled in the art that is able to detect whether a MET mutant according to the present invention is present in a sample. Such methods are known to a person skilled in the art. Non-limiting examples of such assays are in situ hybridization, immunofluorescence microscopy, and confocal microscopy to detect whether a mutant MET protein is located intracellularly. An antibody or an antibody conjugate, may be used to determine whether a mutant MET protein is located intracellularly. A nucleic acid detection technique such as, FISH or FuseFISH (Semrau et al 2014) or an amplification technique such as PCR, rolling circle amplification or NASBA or a nucleic acid based signal amplification technique or a sequencing technique may be used to determine whether a mutant MET is present in a sample. The person skilled in art the is aware of these techniques (see e.g. Green and Sambrook (2012) *Molecular Cloning: A Laboratory Manual*, Fourth Edition, Cold Spring Harbor Laboratory Press, NY). Altogether, a method according to the present invention may comprise analysis of genomic DNA, analysis of mRNA or cDNA, and/or analysis of MET protein in a sample. A mutant MET protein according to the present invention may be the result of a genomic mutation, such as a deletion, and/or may be the result of exon skipping or alternative splicing.

A preferred mutant MET according to the present invention is the result of a chromosomal deletion in chromosome 7, resulting in loss of part of intron 6, exon 7, intron 7 and part of exon 8, thus resulting in a matured mRNA lacking exon 7 and 8 sequences and wherein the mutated MET protein preferably is an uncleaved phosphorylated truncated preform of about 180 kDa. Such mutant MET is herein described in example 1. Preferably, the deletion is about 2114 bp and corresponds substantially to genome positions g. 116395653 and g. 116397766. In the context of these genome positions, the term substantially means that the genome positions may be upstream or downstream of the indicated positions as long as it results in an intact splice donor site of exon 6 and a deletion of splice acceptor sites of exons 7 and 8, making the splice acceptor site of exon 9 the first to accept exon 6. More preferably, the deletion is 2114 bp and corresponds to genome positions g. 116395653 and g. 116397766.

A preferred method according to the present invention involves analysis of genomic DNA to detect a deletion which results in a mutated MET protein according to the present invention. Preferably such deletion is about 2114 bp and corresponds substantially to genome positions g. 116395653 and g. 116397766. In the context of these genome positions, the term substantially means that the genome positions may be upstream or downstream of the indicated positions, as long as it results in an intact splice donor site of exon 6 and a deletion of splice acceptor sites of exons 7 and 8, making the splice acceptor site of exon 9 the first to accept exon 6. More preferably, the deletion is 2114 bp and corresponds to genome positions g. 116395653 and g. 116397766. A preferred version of such method is described in example 1.

A further preferred method according to the present invention involves analysis of mRNA or cDNA to detect a deletion which results in a mutated MET protein according to the present invention. Preferably such deletion is the substantial absence of exons 7 and 8. The substantial absence of exons 7 and 8 is to be construed herein that exons 7 and 8 are absent partly or completely with the result that the encoded protein is a MET mutant protein according to the present invention, A preferred version of such method are described in examples 1 and 2, preferably example 2. Another preferred method is a FuseFISH assay (Semrau et al, 2014). In such FuseFISH assay, two differently colored sets of fluorescent probes are used to discriminate between wild-type MET and a mutant MET according to the present invention. E.g. a FuseFISH assay can be envisaged where a mixture of green fluorescent oligonucleotides is directed to exon 5/6 and a mixture of red oligonucleotides is directed to exons 7/8; the wild type will be detected as both red and green fluorescence (effectively yellow) since both exon 5/6 and 7/8 are present; the mutant MET is lacking exon 7/8 and will be detected as green fluorescent. Such assay can be performed in situ in cells; alternatively an array or chip of colored oligonucleotides can be used and purified RNA be applied. Mutant MET can alternatively be detected on the transcript level in tissue sections by utilizing PADLOCK probes that allow rolling circle amplification of the exons 6-9 junction (Weibrecht et al, 2013).

A further preferred method according to the present invention involves analysis of MET protein to determine whether the MET protein is substantially or exclusively located intracellularly or whether at least part is on the cell surface. Such method may be but is not limited to fluorescence microscopy, confocal microscopy and protein analysis of tissue biopsies, e.g. via SDS-PAGE and western blotting.

A preferred method according to the present invention entails analysis of genomic DNA, mRNA and/or cDNA which involves a nucleic acid detection assay comprising an oligonucleotide, wherein a complex of the oligonucleotide with a template polynucleotide is formed, or involves analysis of MET protein involving application of an anti-MET antibody, wherein a complex of the anti-MET antibody and the MET protein is formed. Preferably, these methods are those described here above. A preferred method according to the invention is an amplification assay, preferably PCR that is able to discriminate between a wild-type MET and a MET that lacks exon 7 and 8 (MET delta 7/8). Such assay is presented in example 2 and involves the amplification of cDNA that is generated from RNA that is isolated from tumor tissue, tumors exosomes, or from blood, preferably from blood platelets from a subject. The RNA can be converted into cDNA directly and subsequently amplified by an enzyme having reverse transcriptase and DNA polymerase activity, such as rTth polymerase. The RNA can first be converted into cDNA by a reverse transcriptase using an oligo-dT primer, or random (hexanucleotide) primers, or a METrev2561 (SEQ ID NO: 22) primer or a METrev2393 (SEQ ID NO: 23) primer. Amplification can be performed using a primer that is able to discriminate between a wild-type MET and a MET lacking exon 7 and 8. A preferred primer is forward primer METFW2033junct6_9 (SEQ ID NO: 21) which was designed such that the 3'six nucleotide motif is specific for exon 9 and the remaining nucleotides are specific for exon 6; the primer thus only anneals to a MET mutant cDNA lacking exon 7 and 8, i.e. anneals on the junction of exon 6 and 9. The persons skilled in the art knows that some variation is possible as long as the primer is specific for the junction of exon 6 and 9. Of course, the same strategy can be used using a reverse primer that is specific for the junction between exon 6 and 9. The forward primer can be used in combination with any suitable reverse primer such as METrev2561 (SEQ ID NO: 22) and METrev2393 (SEQ ID NO: 23). The combination of METFW2033junct6_9 and METrev2393 results in a product of 120 bp when the mutation is present that results in a MET lacking exon 7 and 8; the combination of METFW2033junct6_9 and METrev2561 results in a product of 268 bp when the mutation is present that results in a MET lacking exon 7 and 8. Wild-type MET results in no PCR product. A preferred assay using the primers depicted here is the assay set forward in example 2. Detection of a PCR product may be performed using any means known to the person skilled in the art, such as gel electrophoresis and the use of a detectable probe that is specific for the PCR product, such as a fluorescent capture probe.

A method according to this aspect of the present invention may be performed in vivo, ex vivo, in situ or in vitro. In all aspects and embodiment of the present invention, a sample may be an in vivo, ex vivo, in situ or in vitro sample. The sample may be any sample from a subject that is suitable for a method according to the present invention. Preferred samples comprises a tissue, a tumor tissue, urine, sperm, saliva, blood, blood plasma, cerebrospinal fluid, blood platelets, and/or exosomes. Such sample may already be available; it may be necessary to acquire such sample. Nucleic acid such as DNA, RNA and, cDNA can be isolated and purified from the sample if necessary before a method according to the invention is performed on such nucleic acid.

A method according to the present invention can conveniently be used to determine whether a condition of a subject is susceptible to treatment with a MET activation inhibitor.

Accordingly, in a second aspect, the present invention provides for a method to determine whether a MET associated condition, preferably a cancer, of a subject is susceptible to treatment with a MET activation inhibitor comprising:
 a. providing a sample from the subject, and
 b. performing on the sample according to (a), a method according to the first aspect of the present invention,
wherein the presence of an auto-active and intracellular mutant MET indicates non-susceptibility to a MET activation inhibitor.

A MET activation inhibitor is herein defined as an agent that is capable of inhibiting the process that brings MET into its activated form (see Background section) wherein typically tyrosine (Y) residues 1230, 1234 and 1235 are phosphorylated. Such agent may interfere with or may block binding of the ligand Hepatocyte Growth Factor (HGF) to the extracellular domain of MET. Preferably, a MET activation inhibitor is an antibody against HGF or against the HGF binding site on MET, thus inhibiting or blocking interaction between HGF and MET, thereby preventing MET activation. A preferred MET activation inhibitor is not a tyrosine kinase inhibitor. Preferred MET activation inhibitors are those described in Surati et al, 2011 and Godzik-Spychalski et al, 2014, such as MetMAb and AMG102 (Rilotumumab).

It is evident that the presence of an auto-active and intracellular mutant MET indicates non-susceptibility to a MET activation inhibitor since the mutant MET does not require activation by e.g. binding of HGF.

A method according to this aspect of the present invention may be performed in vivo, ex vivo, in situ or in vitro. In all aspects and embodiment of the present invention, a sample may be an in vivo, ex vivo, in situ or in vitro sample. The sample may be any sample from a subject that is suitable for a method according to the present invention. Preferred samples comprises a tissue, a tumor tissue, urine, sperm, saliva, blood, blood plasma, cerebrospinal fluid, blood platelets, and/or exosomes. Such sample may already be available; or it may be necessary to acquire such sample.

A method according to the first and second aspect of the present invention can conveniently be implemented in a method of treatment of a subject that has a MET associated condition or is at risk of a MET associated condition.

Accordingly, in a third aspect the present invention provides for a method for the treatment of a MET associated condition, preferably a cancer, of a subject comprising: requesting performance or performing a method according to the first or second aspect of the invention on a sample of the subject, thus determining susceptibility of the condition of the subject to a MET activation inhibitor, and treating a subject with a MET associated condition that is susceptible to a MET activation inhibitor by administration of a therapeutically effective amount of at least one MET activation inhibitor and/or treating a subject with MET associated condition that is non-susceptible to a MET activation inhibitor by administration of a therapeutically effective amount of at least one alternative medicament, preferably a tyrosine kinase inhibitor.

In the context of all embodiments of the present invention, an alternative medicament is any medicament that is not a MET activation inhibitor as defined herein that interferes with the activity of MET by either acting directly on MET or acting in a MET signaling pathway such as AKT phosphorylation, RAS and pI3K activation, MAPK activation. Such alternative medicament according to the present invention is preferably a tyrosine kinase inhibitor.

The subject may be healthy subject, a subject at risk of a MET associated condition, or may suffer from a MET associated condition.

In addition, in a third aspect the present invention provides for a medicament for use in the treatment of a MET associated condition, preferably a cancer, of a subject in need thereof, wherein:
 a. a method according to the first or second aspect of the present invention on a sample of the subject is performed or requested to be performed, thus determining susceptibility of the condition of the subject to a MET activation inhibitor, and
 b. administration to a subject with a MET associated condition that is susceptible to MET activation inhibitor of a therapeutically effective amount of at least one medicament which is a MET activation inhibitor and/or administration to a subject with MET associated condition that is non-susceptible to a MET activation inhibitor of a therapeutically effective amount of at least one alternative medicament which is not a MET activation inhibitor, preferably a tyrosine kinase inhibitor.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission. "Treatment" can also mean prolonging survival as compared to expected survival if not receiving treatment. The term "prevention" or "prophylaxis", or synonym thereto, as used herein refers to a reduction in the risk or probability of a patient develop a disease, preferably a MET associated condition according to the present invention.

The term a "therapeutically effective amount", "effective amount" or a "sufficient amount" of a compound of the present invention is a quantity sufficient to, when administered to the subject, including a mammal, for example a human, obtain beneficial or desired results, including clinical results, and, as such, an "effective amount" or synonym thereto depends upon the context in which it is being applied. In the context of disease, therapeutically effective amounts of the compounds of the present invention are used to treat, modulate, attenuate, reverse, or effect a MET associated condition in a mammal. An "effective amount" is intended to mean that amount of a compound that is sufficient to treat, modulate, attenuate, reverse, or effect a MET associated condition in a mammal.

In the context of all embodiments of the present invention, a MET associated condition is any condition that is associated with an aberrant MET wherein an aberrant MET is any MET that is aberrant as compared to normal conditions and preferably involves a mutation of MET, a polymorphism of MET, loss of heterozygosity, duplication or deletion of MET or of its locus or a part thereof and overexpression of MET. A MET associated condition may be any such condition known to the person skilled in the art. A MET associated condition that is non-susceptible to a MET activation inhibitor is preferably a condition associated with an auto-active and intracellular MET mutant according to the present invention. A MET associated condition according to the present invention may be a cancer, but may also be another condition. Preferably, the MET associated condition is amyotrophic lateral sclerosis, systemic sclerosis, ulcerative colitis, autism and/or a cancer selected form the group consisting of lymphoma, leukemia, mycosis fungoide, carcinoma, adenocarcinoma, sarcoma, rhabdomyosarcoma, Ewing sarcoma, castration resistant prostate carcinoma, glioma, astrocytoma, blastoma, neuroblastoma, plasmacytoma, histiocytoma, melanoma, adenoma, hypoxic tumour, myeloma, metastatic cancer, bladder cancer, brain cancer, nervous system cancer, squamous cell carcinoma of the head and neck, neuroblastoma, glioblastoma, ovarian cancer, skin cancer, liver cancer, squamous cell carcinomas of the mouth, throat, larynx, and lung, colon cancer, cervical cancer, breast cancer, cervical carcinoma, epithelial cancer, renal cancer, genitourinary cancer, pulmonary cancer, esophageal carcinoma, lung cancer, head and neck carcinoma, hematopoietic cancer, testicular cancer, colorectal cancer, prostatic cancer, and pancreatic cancer.

In a method according to the third aspect of the present invention, the sample may be an in vivo, ex vivo, in situ or in vitro sample. The sample may be any sample from a subject that is suitable for a method according to the present invention. Preferred samples comprises a tissue, a tumor tissue, urine, sperm, saliva, blood, blood plasma, cerebrospinal fluid, blood platelets, and/or exosomes. Such sample may already be available; it may be necessary to acquire such sample.

In a fourth aspect, the present invention provides for a biomarker for determining the presence of a MET mutant in a sample, wherein the MET mutant is an auto-active and intracellular mutant MET and wherein the biomarker preferably is an oligonucleotide or a set of oligonucleotides, an antibody or conjugates thereof or an array or chip comprising a multiplicity of such biomarker.

The biomarker may be any biomarker capable of detecting an auto-active and intracellular mutant MET. The person skilled in the art knows how to provide such biomarker and how to use it.

A preferred biomarker according to the present invention is an oligonucleotide that can hybridize to SEQ ID NO: 15 or its reverse complement. Such oligonucleotide can conveniently be used in a nucleic acid detection technique such as, FISH or FuseFISH (Semrau et al 2014) or an amplification technique such as PCR or NASBA or a nucleic acid based signal amplification technique or a sequencing technique. A further preferred oligonucleotide according to the present invention for the detection of an auto-active and intracellular mutant MET is an oligonucleotide that can hybridize to exon 6 (SEQ ID NO: 16) and/or exon 9 (SEQ ID NO: 17) or its reverse complement; a set of such oligonucleotides can e.g. conveniently be used for PCR or RT-PCR. A further preferred oligonucleotide according to the invention is an oligonucleotide that hybridizes to the boundery between intron 6-7 (SEQ ID NO: 17) or its reverse complement and exon 8 (SEQ ID NO: 18) or its reverse complement, of the aberrant MET delta 7/8. Such oligonucleotide according to the present invention can conveniently be used for e.g. FISH. A further preferred oligonucleotide according to the present invention is capable hybridize to a sequence within exon 6 (SEQ ID NO: 16), intron 6-7 (SEQ ID NO: 17), exon 8 (SEQ ID NO: 18), intron 8-9 (SEQ ID NO: 19) and/or exon 9 (SEQ ID NO: 20), or a reverse complement thereof. A further preferred oligonucleotide according to the present invention is an oligonucleotide as defined in the examples, such as MET1997Fw (SEQ ID NO: 5), MET2342Rv (SEQ ID NO: 6) and MET2414Rev (SEQ ID NO: 8). A preferred set of oligonucleotides is MET1997Fw (SEQ ID NO: 5) and MET2342Rv (SEQ ID NO: 6); a further preferred set is MET1997Fw (SEQ ID NO: 5) and MET2414Rev (SEQ ID NO: 8). An oligonucleotide according to the present invention may comprise or may not comprise a recognition site for a restriction enzyme. An oligonucleotide according to the present invention preferably is an oligonucleotide comprising or consisting of from 15 to 100 nucleotides, more preferred from 15 to 30 nucleotides or preferably comprising or consisting of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. In an oligonucleotide according to the present invention, the complementarity to hybridization counterpart preferably is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc. The complementary part of an oligonucleotide according to the present invention may be flanked by an oligonucleotide part or parts comprising of e.g. 1, 2, 3, 4, 5, 6, 7, 8, 9 or 10 nucleotides that is or are not complementary and may be unrelated to MET.

A preferred biomarker is used in a kit, comprising multiple oligonucleotides, preferably e.g. 20, which are designed to specifically hybridize in array to MET sequences, except for exon?/8-encoded sequences, and labeled with a fluorophore which emits green fluorescent light, and multiple oligonucleotides, preferably 20, specifically hybridizing in array to exon 7/8 sequences of MET mRNA and labeled with a fluorophore which emits red fluorescent light. Contacting this panel with RNA in tissue sections in an in situ hybridization experiment, will reveal presence of MET as yellow spots and MET mutant as green spots in individual cells.

In a fifth aspect, the present invention provides for a kit for determining the presence of a MET mutant in a sample, wherein the MET mutant is an auto-active and intracellular mutant MET, comprising at least a biomarker as defined in the fourth aspect of the present invention and instructions for use.

Such kit according to the present invention can conveniently be used for determining the presence of a MET mutant in a sample, wherein the MET mutant is an auto-active and intracellular mutant MET. Such use preferably involves a method as defined previously herein.

In a sixth aspect, the present invention provides for a polynucleotide encoding a MET mutant as defined in the first aspect of the present invention or a part thereof, or a MET mutant protein as defined in the first aspect of the present invention, or a part thereof. A preferred MET mutant protein is a protein or a part thereof with a sequence identity of at least 80%, 85%, 90%, 91%, 92%, 93%, 94%, 95%, 96%, 97%, 98%, 99%, 100% with the polypeptide sequence as set forward in SEQ ID NO: 13. A more preferred MET mutant protein has the polypeptide sequence as set forward in SEQ ID NO: 13.

Herein, a polynucleotide is represented by a nucleotide sequence. A polypeptide is represented by an amino acid sequence. The term "polypeptide" or "protein" as used herein refers to any peptide, oligopeptide, polypeptide, or protein. A polypeptide is comprised of consecutive amino acids. The term "polypeptide" encompasses naturally occurring or synthetic molecules. The term "polynucleotide" as herein refers to RNA, DNA, and cDNA molecules. The term is used interchangeably with polynucleotide. An oligonucleotide is a short chain nucleic acid molecule, preferably consisting of at most 100 nucleotides. A primer is an oligonucleotide which is capable of acting as a point of initiation of synthesis when placed under conditions in which synthesis of a primer extension product which is complementary to a nucleic acid strand is induced, (i. e. in the presence of nucleotides and an inducing agent such as DNA polymerase and at a suitable temperature and pH). The primer is preferably single stranded for maximum efficiency in amplification.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 1% of the value.

The sequence information as provided herein should not be so narrowly construed as to require inclusion of erroneously identified bases. The skilled person is capable of identifying such erroneously identified bases and knows how to correct for such errors.

All patent and literature references cited in the present specification are hereby incorporated by reference in their entirety.

TABLE 1

Sequences as set forth in the Sequence Listing

| SEQ ID NO: | SEQ type | Description |
|---|---|---|
| 1 | PCR primer | HGF-Fw204 |
| 2 | PCR primer | HGF-Rv504 |
| 3 | PCR primer | p361-Fw |
| 4 | PCR primer | P425-Rv |
| 5 | PCR primer | MET1997Fw |
| 6 | PCR primer | MET2342Rv |
| 7 | PCR primer | MET1997Fw |
| 8 | PCR primer | MET2414Rev |
| 9 | PCR primer | MET173EcoR1-Fw |
| 10 | PCR primer | MET4421NotI-Rv |
| 11 | PCR primer | MET173Fw |
| 12 | PCR primer | MET3028NheI-Rv |
| 13 | PRT | MET wild-type |
| 14 | PRT | MET delta 7/8 |
| 15 | DNA | MET delta 7/8 exon 6 <-> exon 9 |
| 16 | DNA | MET delta 7/8 exon 6 |
| 17 | DNA | MET delta 7/8 intron 6-7 |
| 18 | DNA | MET delta 7/8 exon 8 |
| 19 | DNA | MET delta 7/8 intron 8-9 |
| 20 | DNA | MET delta 7/8 exon 9 |
| 21 | DNA | METFW2033junct6_9 |
| 22 | DNA | MET2561R |
| 23 | DNA | MET2393R |

FIGURE LEGENDS

FIG. 1. MET is constitutively activated in the E98 cell line and xenograft model A) Sections of an intracranial E98 xenograft were subjected to immunohistochemistry for P-MET (brown staining). Note that tumor shows diffuse infiltration in the brain parenchyma and that the tumor cells are highly positive for this activated MET.

B) Western blot analysis of MET expression in serum-starved E98 and A549 cells in absence of presence of HGF. Note that the processed form of MET (arrowhead) in E98 is somewhat smaller than that of A549 while the preform is predominantly present in E98 (arrow). α-tubulin was used as a loading control.

C) RT-PCR for HGF on E98, TOV-112D and HEK-293T cell line cDNA. HMBS was used as a control housekeeping gene.

FIG. 2. E98 MET contains an intronic deletion, resulting in a truncated transcript A) RT-PCR on cDNA from different cell lines using full length MET primers, using HMBS as a housekeeping gene for reference.

B) Ion-torrent sequencing analysis exposes a high-copy amplification of MET in E98 DNA. Plotted on the x-axis are all 409 genes sequenced, in chromosomal order. The number of reads per gene was compared to blood-obtained DNA from a glioma patient as a reference. The dotted line represents the level of heterozygous losses, as can be seen for the X-chromosome (the reference blood sample was female, while the tumor DNA was male). The inset shows the relative number of reads per MET exon. Note the loss of exon 7 and part of exon 8.
C) FISH analysis of the number of MET (red) and chr. 7 centromere (green) copies in the genome of an E98 xenograft. D) Amplification of MET using exon 6 and 9-specific primers on genomic DNA of E98 and U87 cells. METAΔ7-8 and wtMET amplification leads to 910 and 3041 bp products in E98 and U87 respectively.
D) Schematic overview of the METΔ7-8 deletion found in E98 cDNA. Splicing of exon 6 to exon 9 is indicated with the dotted orange lines. The orange solid line represents the deletion.

FIG. 3. Predicted protein structure of METΔ7-8
A) Schematic overview of MET and METΔ7-8. The red lined box represents the deletion, comprising parts of the IPT1 and 2 domains (represented by the red and yellow boxes respectively in METΔ7-8).
B) Yasara modeling of the remaining IPT1 and 2 domains in METΔ7-8 was performed based on wtMET IPT1. The wtMET SEMA domain and IPTs are shown in blue, with the novel putative IPT domain consisting of IPT1 (red) and 2 (yellow) of METΔ7-8, superimposed on wtMET. An enlargement of the fusion part in the overview figure (arrow) is shown in the right panel. The arrow indicates the additional loop in red that is formed by the novel IPT domain.

FIG. 4. Aberrant processing and localization of METΔ7-8
A) Western blot analysis of MET expression in HEK-293T and TOV-112D cells, transfected with pIRESneo-MET or pIRESneo-METΔ7-8. Note that HEK-293T cells have endogenous MET expression. As a loading control, α-tubulin was used.
B) Analysis of MET localization in E98 by confocal microscopy, using CD44 as a membrane marker (green) in combination with C-terminal MET antibodies (red), or phosphorylated MET (1234/1235, red) as indicated. U87 cells were also analyzed for MET/CD44 colocalization for comparison. Q-nuclear deep red stain was used to stain all nuclei.
C) Subcellular localization of MET (green) with early endosome and RER markers EEA-1 and CLIMP-63 (both in red).
D) Western blots of biotinylated E98 and A549 cells or cell lysates. MET was immunoprecipitated and analyzed on western blot for biotinylation. The α-chain of MET is shown.
E) His-tagged ectodomains of both wildtype MET and METΔ7-8, biotinylated via a biotin-acceptor peptide at the carboxyterminus, were expressed in HEK-293T cells. Ni-purified culture media and extracts of the transfected cells were used to analyze MET localization. Both fractions were subjected to western blotting using N-terminal MET antibodies, recognizing both the preform and the cleaved α-portion of the ectodomain, and directly labeled streptavidin to visualize the preform and the n-chain. GAPDH was used as a loading control for the RIPA extracts (red signal at 36 KDa).

Figure 5:
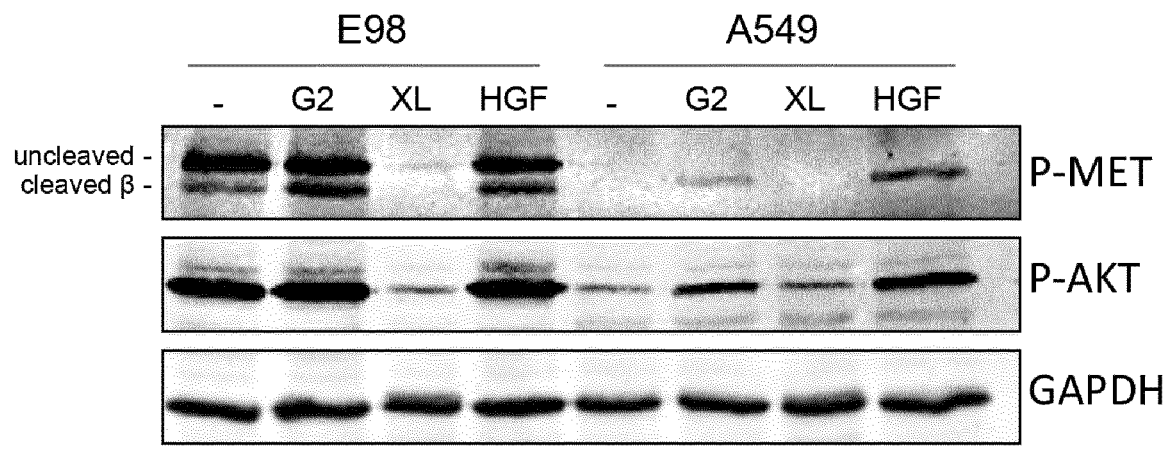

FIG. 5. METΔ7-8 is blocked by TKIs but not by inhibiting antibodies E98 and A549 cells were left untreated or treated with the MET VHH G2, cabozantinib (XL; MET/VEGFR2 inhibitor), or HGF. Protein lysates were analyzed for MET and AKT phosphorylation. GAPDH was used as a loading control. Note the prominent uncleaved MET protein in E98, which is absent in A549 cells.

FIG. 6. METΔ7-8 is expressed in glial tumors
A) PCR analysis of cell line cDNAs using primers located in exon 6 and exon 9. This PCR results in a product of 105 bp for the METΔ7-8, while wtMET gives a 345 bp product.
B) Immunohistochemical staining for MET of the patients' tumor from which the E98 cell line has been generated.
C) FISH analysis of the number of MET (red) and chromosome 7 (green) copies in the original E98 patient tumor. D) PCR analysis for. METΔ7-8 on a random set of glioma and NSCLC biopsies. Note that in tumors with METΔ7-8 expression, also wtMET is observed.

Figure 7:
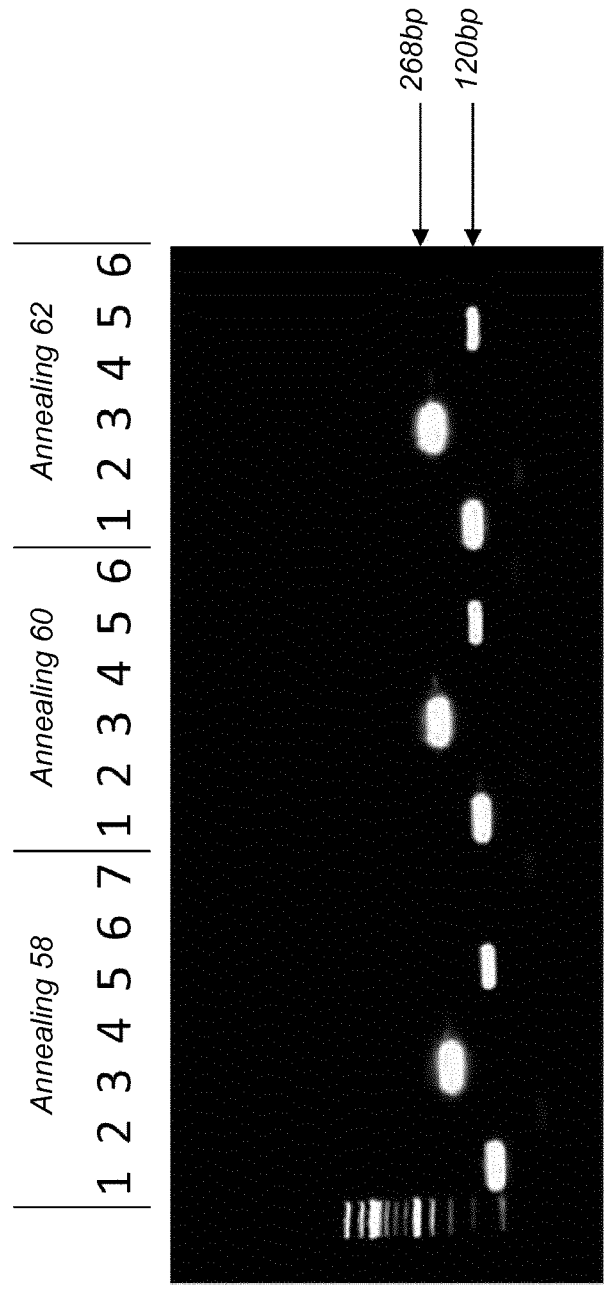

FIG. 7. Discriminative PCR for the detection of MET RNA lacking exon 7 and 8 (METΔ7-8).
PCR analysis of wild-type MET cDNA and MET A7-8 cDNA. When using primer pair METFW2033junct6_9 and MET2393R, a PCR product of 120 bp is generated from MET. Δ7-8 cDNA, no PCR product is generated from wild-type MET. Likewise, when using primer pair METFW2033junct6_9 and MET2561R, a PCR product of 268 bp is generated from MET A7-8 cDNA, no PCR product is generated from wild-type MET.

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual ($2^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 or Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

EXAMPLES

Example 1. A novel MET mutation in high-grade glioma and non-small cell lung carcinoma resulting in an auto-active intracellular protein
Abstract
MET is a tyrosine kinase membrane receptor that has gained interest as a therapeutic target for a number of malignancies, including glioma, because of its involvement in tumorigenesis, invasion and metastasis. At present, a number of inhibitors, both antibodies against MET or its ligand hepatocyte growth factor (HGF), and small molecule MET tyrosine kinase inhibitors are in clinical trials.
We here describe a novel mutation in MET that we found to be present in 6% of high-grade gliomas and 14% of non small cell lung carcinomas. Characterization of this mutation in a glioma cell line revealed that it consists of an intronic deletion, resulting in a splice event connecting an intact splice donor site in exon 6 with the next splice acceptor site being that of exon 9. The encoded protein lacks parts of the extracellular IPT-domains 1 and 2, encoded by exons 7 and 8, and is named METΔ7-8. As a result of the mutation, METΔ7-8 is located predominantly in the cytosol where it is constitutively active, independent of the presence of HGF. The auto-activating nature of this protein, in combination with a lack of transmembrane localization, renders METΔ7-8 not targetable using antibodies. Genetic testing of MET-expressing tumors for the presence of this variant is therefore warranted for treatment decision making.
Introduction
The MET proto-oncogene (chromosome 7q31.2) encodes the tyrosine kinase membrane receptor MET (also called Scatter Factor Receptor), which is essential during development. Signaling from the receptor controls epithelial-to-mesenchymal transition (EMT) of myogenic precursor cells during differentiation into skeletal muscle cells (Bladt et al., 1995), a process that involves migration over long distances in the embryo. In adults, MET is involved in tissue regeneration upon injury (Borowiak et al., 2004; Chmielowiec et al., 2007; Huh et al., 2004).

MET is produced as a glycosylated single chain precursor protein of ~190 kDa which, during transport to the membrane, undergoes furin-mediated cleavage in the trans-Golgi network (Komada et al., 1993). The resulting mature receptor consists of an extracellular 50 kDa α-chain, covalently attached via a disulfide bond to a membrane-spanning 140 kDa β-chain (Chan et al., 1988; Liu et al., 1996; Park et al., 1987). The extracellular segment consists of an N-terminal Sema-domain that is involved in ligand binding, a small cysteine-rich domain, and four IPT (Immunoglobulin-like fold shared by Plexins and Transcription factors) domains, which connect the Sema and cysteine-rich domains with the C-terminal β-subunit (Gherardi et al., 2003).

Upon binding of the ligand Hepatocyte Growth Factor (HGF, Scatter Factor), receptor dimerization occurs followed by trans-phosphorylation in the intracellular tyrosine kinase (TK) domain at tyrosine (Y) residues 1230, 1234 and 1235 (Ferracini et al., 1991; Longati et al., 1994). The TK domain subsequently induces autophosphorylation of Y1349 and Y1356 which act as docking sites for signal transduction molecules including GAB1, GRB2, phospholipase-C and SRC (Ponzetto et al., 1994). Phosphorylated GAB1 interacts with molecules like PI3-K and SHP2 which together induce several downstream signaling pathways. MET signaling is mediated by, among others, the PI3-K/AKT and RAS/MAPK pathways, which induce cell cycle progression, survival, cytoskeletal changes and invasion (Gherardi et al., 2012). In addition to its role downstream of HGF, MET can also be involved in signaling of other transmembrane receptors, including VEGFR2, CD44, and Plexin B1 (Lai et al., 2009; Lu et al., 2012). Upon ligand-induced receptor dimerization, MET is internalized via endocytosis and may be recycled (Joffre et al., 2011). Phosphorylation of Y1003 in the juxtamembrane (JM) domain of the receptor leads to ubiquitination and subsequent proteasomal degradation (Hammond et al., 2001; Jeffers et al., 1997; Peschard et al., 2001). Thus, levels of MET in the cell are tightly regulated.

Aberrant activation of MET signaling is a tumor promoting event in a variety of malignancies and can be induced by several mechanisms including overexpression of its ligand and/or the receptor itself, alternative mRNA splicing and crosstalk with other receptors (Corso and Giordano, 2013). MET amplifications have been found in a number of tumor types including glioblastoma (GBM) (Cancer Genome Atlas Research, 2008; Sottoriva et al., 2013) whereas missense mutations in the Sema, the TK and the JM domain have been reported to affect HGF binding, kinase activation and receptor degradation, respectively (Asaoka et al., 2010; Kong-Beltran et al., 2006; Lee and Yamada, 1994; Ma et al., 2005; Ma et al., 2008; Onozato et al., 2009; Peschard et al., 2001; Petrelli et al., 2002).

The significant role that MET plays in tumor progression and metastasis has made it a prime therapeutic target in oncology. MET tyrosine kinase inhibitors and therapeutic antibodies against the extracellular domain of MET and against HGF, all preventing HGF-mediated MET activation, are currently in clinical trial (www.clinicaltrials.gov). In a previous study we have shown that the combined VEGFR2/MET tyrosine kinase inhibitor cabozantinib (XL-184, CoMETRIQ) potently inhibits MET phosphorylation, cell proliferation and migration and consequently prolongs survival of mice carrying orthotopic E98 GBM xenografts. Here we identify a novel MET mutation which results in a truncated protein that is constitutively active and lacks membranous expression, thereby having important implications for therapeutic strategies targeting MET.

Methods

Cell Lines and Xenografts

The E98 cell line and xenograft model and genetic analysis thereof have been described before (Caretti et al., 2011; Claes et al., 2008). E98, U87, A549, HEK-293T and TOV-112D cells were cultured in DMEM+4.5 g/L glucose medium (PAA Laboratories, Pasching, Austria) supplemented with 10% fetal calf serum (FCS) (PAA) and gentamycin (40 µg/mL). All cell lines were maintained at 37° C. in the presence of 5% CO2. To examine HGF-induced MET activation, E98 and A549 cells were seeded in 6 wells plates. The next day cells were serum-starved overnight. The following day cells were treated for 10 minutes (min) with HGF (50 ng/mL, Miltenyi Biotec, Bergisch Gladbach, Germany). In some experiments, prior to HGF incubation cells were incubated with the anti-MET llama VHH G2 (Heukers et al., 2014) or cabozantinib (XL-184, Exelixis, San Francisco, Calif.) for 60 min.

Protein Expression Analysis

Cell lysates were prepared using RIPA buffer containing protease and phosphatase inhibitors (Cell Signaling Technology, CST, Danvers, Mass., USA). RIPA extracts (20-40 µg per lane) and His-tagged proteins from conditioned media (equivalent of 20 µl conditioned medium) were subjected to PAGE on 8-10% polyacrylamide gels and western blotting according to standard procedures. Nitrocellulose blots (Whatman Optitran BA-S85, GE Healthcare, Little Chalfont, UK) were blocked with PBS/Odyssey Blocking Buffer (LI-COR Biosciences, Lincoln, Nebr., USA) (1:1), followed by overnight incubation with primary antibodies at 4° C. Antibodies used were against MET N-terminus (clone EP1454Y, Epitomics, Abcam, Cambridge, UK), MET C-terminus (clone D1C2), phosphorylated (P)-MET (Y1234/1235, clone D26) (CST), GAPDH (clone 6C5, Abcam), and α-tubulin (clone 236-10501, Molecular Probes, Life Technologies). Biotin groups and primary antibodies were visualized using respectively streptavidin-680 (Molecular Probes, Life Technology) and appropriate secondary antibodies [goat-anti-rabbit-IRDye800 (Rockland Immunochemicals, Gilbertsville, Pa., USA) or Alexa Fluor 680 goat-anti-mouse IgG (Molecular Probes, Life Technologies)]. Blots were scanned on the Odyssey imager (LI-COR Biosciences).

Immunohistochemistry

Immunohistochemistry on formalin fixed paraffin embedded (FFPE) slides was performed as previously described (Navis et al., 2011), using antibodies against MET and P-MET (clone D1C2 and D26 respectively, both CST). Bound antibodies were visualized via sequential incubations with biotinylated secondary antibodies, avidin-biotin complexes (Vector laboratories, Burlingame, Calif., USA) and 3,3'-diaminobenzidine solution (Power-DAB, Immuno-Logic, Duiven, The Netherlands).

RNA Analysis

RNA was isolated from cell lines using TRIzol Reagent (Life Technologies) according to the manufacturer's instruction. Glioma tissues were in part obtained from the Radboud UMC and from the University of Cologne (n=80). Sarcoma (n=25) and castration resistant prostate cancer (CRPC) tissues (n=43) were obtained from the Radboud UMC. Non small cell lung cancer (NSCLC) samples were obtained from the VU University Medical Centre Amsterdam. For RNA isolation from tissues, the mirVANA RNA isolation kit was used (Life Technologies), according to standard procedures. For cDNA synthesis, 1 µg RNA was transcribed using oligo-dT primers (Invitrogen, Carlsbad, Calif., USA) or via the Quantitect Reverse Transcription Kit (QIAGEN, Venlo, The Netherlands), containing both oligo-dT and random primers. HGF was PCR-amplified using Phusion High-Fidelity DNA polymerase (Finnzymes, ThermoFisher Scientific, Waltham, USA) according to the manufacturers' instructions. Primers were HGF-Fw204 (5'-CTGCAG-CATGTCCTCCTGCA-3'; SEQ ID NO: 1) and HGF-Rv504 (5'-GAGGTCAAATTCATGGCCAA-3'; SEQ ID NO: 2) (30 cycles, annealing at 55° C., 20 sec; extension at 72° C., 20 sec). Control PCR reactions were performed for housekeeping gene HMBS (Hydroxymethylbilane Synthase) (Chretien et al., 1988), using primers p361-Fw (5'-TGCCAGAGAAGAGTGTGGTG-3'; SEQ ID NO: 3) and p425-Rv (5'-GTTAAGCTGCCGTGCAACATC-3'; SEQ ID NO: 4) primers. To distinguish wtMET from METΔ7-8-transcripts, a PCR was performed in AmpliTaq Gold 360 mastermix (Applied Biosystems, Life Technologies) using primer MET1997Fw (5'-CTCCTTGGAAATGAGAGCTG-3'; SEQ ID NO: 5, forward, located in exon 6), and primer MET2342Rv (5'-CAGTTGAAATGGTTTGGGCTG-3'; SEQ ID NO: 6, reverse, located in exon 9). This PCR results in a 105 bp product for METΔ7-8 and a 345 bp product for wtMET. Conditions were: denaturation 95° C., followed by 35 cycli of 95° C. denaturation; annealing at 58° C., 30 sec; elongation at 72° C., 1 min. A final elongation step of 7 min was done at 72° C.

Genetic Analysis

DNA was isolated from E98 cells using the DNeasy Blood & Tissue Kit (QIAGEN), according to the manufacturer's protocol. 10 ng was subjected to PCR, using primer MET1997Fw (5'-CTCCTTGGAAATGAGAGCTG-3; SEQ ID NO: 7, forward, exon 6, genome location chr7q; g116395517-36) and a reverse primer MET2414Rev (5'-GGGATCTTCACGGTAACTG-3'; SEQ ID NO: 8, located in exon 9, CHR7q; g. 116398565-45).

E98 was genetically analyzed by semi-conductor sequencing (IonPGM, Life Technologies) using the comprehensive cancer panel (Life Technologies) that targets 409 cancer-related genes. The IonPGM E98 library generation was performed according to the manufacturer's protocol. In short, 10 ng of DNA per pool, was amplified in 21 cycles by PCR using the Ion AmpliSeq™ mastermix, followed by barcode and adapter ligation. Amplified products were purified with Agencourt AMPure XP beads (Beckman Coulter Genomics, High Wycombe, UK). The library was diluted to 20 pM. Emulsion PCR was performed using the Ion OneTouch™ 200 Template kit following the protocol of the Ion OneTouch™ System. Next, Ion Sphere Particles (ISPs) were recovered and enriched for template positive ISPs using Dynabeads MyOne Streptavidin C1 beads (Life Technologies) in the Ion OneTouch™ ES instrument (Life Technologies). ISP enrichment was quantified using the Qubit 2.0 fluorometer (Life Technologies). Sequencing primer and polymerase were added to the final enriched spheres before loading onto an Ion 318 chip according to the Ion PGM™ 200 sequencing kit protocol. The gene copy number analysis was performed as follows. The relative number of sequence reads aligned to a specific gene (of the total number of aligned reads of E98) was determined for each gene and divided over the relative number of sequence reads aligned to a specific gene (of the total number of aligned reads of an unrelated blood sample). The relative ratios are plotted in a graph based on the genomic position of the gene.

Fish

FFPE sections (4 µm) on SuperFrost glass. (dried>45 min at 56° C.) were deparaffinized and rehydrated in ddH2O. After boiling in a microwave in sodiurncitrate buffer (pH 6), slides were allowed to cool to RT, washed in ddH2O and incubated for 5 min in 10 mM HCl. Proteins were digested with pepsin (200 U/mL, Sigma) for 15 min at 37° C. Subsequently, slides were rinsed in 10 mM HCl and PBS and postfixed for 5 min in 1% paraformaldehyde (PFA, Merck)/PBS. Sections were washed in ddH20, dried and hybridized with 10 µl probe mix (1 µl cep7 Spectrum Green (06J37007)+1 µl LSI MET Spectrum Red (06N05-001)+7 µl hybridization buffer in MQ, all Vysis) under a cover slip. Sections were denatured at 80° C. for 10 min, followed by hybridization o/n at 37° C. in a Hybridizer (Dako). After removing the coverslip by soaking for 5 min in 2×SSC buffer (Maxim Biotech) at 42° C. slides were washed 3 times in 2×SSC buffer at 73° C., once in 2×SSC (5 min) and once in ddH2O. After dehydration in EtOH, slides were air-dried in the dark and mounted in Vectashield/DAPI (3 parts Vectashield/DAPI+1 part Vectashield, all Vector). Slides were analyzed on a Leica Fluorescence microscope.

Protein Domain Modeling

A homology model for the new hybrid IPT-domain using the WHAT IF & YASARA Twinset was generated (Krieger et al., 2002; Vriend, 1990). We used the experimentally solved 3D-structure 2uzx, which contains the human tyrosine kinase MET. The first 60 residues of the hybrid domain are identical to this structure, whereas the following 38 residues were modeled based on homology between the 2 domains.

Cloning

The METΔ7-8 open reading frame was PCR amplified (Phusion DNA polymerase, Finnzymes) from E98 cDNA using primers flanking the start and stop codons (MET173EcoR1-Fw: 5'-CGAATTCGATAAACCTCTCAT-AATGAAGG-3'; SEQ ID NO: 9 and MET4421NotI-Rv 5'-AGCGGCCGCCTATGATGTCTCCCAGAAGG-3'; SEQ ID NO: 10). The 3,961 bp PCR product was purified, digested with NotI and cloned as blunt-NotI fragment in pIRESneo-EcoRV-NotI (Clontech Laboratories, Inc, CA, USA). wtMET cDNA was PCR-cloned from the MET overexpressing ovary carcinoma cell line TOV-112D-MET using MET173Fw (5'-GATAAACCTCTCATAAT-GAAGGC-3'; SEQ ID NO: 11) and MET4421NotI-Rv. The extracellular parts of METΔ7-8 and wtMET were PCR-amplified from cDNA using primers MET173EcoR1-Fw and MET3028NheI-Rv (5'-CGCTAGCCTGATCTGGTT-GAACTATTAC-3'; SEQ ID NO: 12), and cloned in vector pHLsec-BAPHIS, a derivative from pHLsec-HIS (Addgene, Cambridge, Mass., USA). The resulting vector adds a biotin-acceptor peptide and His-tag to the carboxyterminus of the MET extracellular domains, thus resulting in pHLsec-METΔ7-8ED-BAPHIS and pHLsec-METED-BAPHIS.

Transfection pIRESneo-MET or pIRESneo-METΔ7-8 were transfected into HEK-293T or TOV-112D cells in 6-well culture dishes (Greiner Bio-One, Krëmsmunster, Austria) using Fugene HD transfection reagent (Promega, Fitchburg, Wis., USA) according to the manufacturer's instructions. After 48 hrs, cell monolayers were washed with PBS and cell extracts prepared in RIPA buffer. In separate experiments, pHLsec-METΔ7-8ED-BAPHIS or pHLsec-METED-BAPHIS were cotransfected in a 1:1 ratio with the, biotin-ligase expression construct pDISPLAY-BirA-ER (Addgene) and cells were cultured in the presence of 10 µM biotin (Sigma-Aldrich, St Louis, Mo., USA). After 48 hours cytosolic extracts were made in RIPA buffer, and His-containing proteins were purified from the conditioned media using Nickel beads. 100 ul Ni-NTA sepharose slurry (IBA, Goettingen, Germany) was incubated with 1 ml conditioned medium for 1 hour at 4° C. After 3 washes with buffer (500 mM NaCl, 50 mM phosphate buffer, pH 7.4) beads were loaded onto a Poly-Prep column (Bio-Rad, Hercules, Calif., USA) and aspecifically bound proteins were eluted with 2 ml 10 mM imidazole. Finally, protein constructs were eluted with 0.5 ml 0.5 M imidazole, and dialysed o/n at 4° C. to 50 mM TRIS/150 mM NaCl pH 7.5.

Confocal Microscopy

E98 and U87 cells, grown on Nunc Lab-Tek chamber slides (Sigma-Aldrich) to 40% confluence, were fixed with 2% PFA in 0.1 M phosphate buffer (pH 7.4) for 15 min at RT, followed by three washes with PBS, 30 min glycine incubation (100 mM in PBS) to quench PFA-induced autofluorescence, three PBS washes and permeabilization with digitonin for 10 min (100 µM in PBS). Aspecific binding was blocked by incubation with 20% normal goat serum in PBS/1% BSA for 20 min, and cells were incubated overnight at 4° C. in a humidified chamber with PBS/1% BSA containing (combinations of): mouse monoclonal anti-CD44 antibody (as a surface marker, clone Hermes-1, ThermoFisher Scientific); rabbit anti-MET (clone D1C2, CST); rabbit anti-P-MET (clone D26, CST); mouse anti-EEA-1 (clone 14/EEA1, BD Biosciences, early endosome marker); anti-CLIMP-63 (clone G1/296, rough ER marker, a kind gift of J. Fransen). Primary antibodies were detected using Alexa Fluor 488- or 594-labeled secondary goat-anti-mouse and Alexa Fluor 488- or 568-labeled goat-anti-rabbit IgGs (all Life Technologies), 1:200 diluted in PBS/1% BSA. Q-nuclear deep red (1:200, Life Technologies) was used to stain nuclei, and cells were mounted in Fluoromount G with DAPI (Southern Biotech, Birmingham, Ala., USA). Cells were analyzed using a confocal laser scanning microscope (Leica SP2 CLSM) and Leica confocal software.

Biotinylation Assay

E98 and A549 cells were allowed to adhere for 24 hrs until 80% confluence in a 6-wells plate (Cellstar, Greiner Bio-One, Kremsmünster, Austria), washed 3× with ice cold PBS and incubated for 30 min at 4° C. with 0.5 mg/ml EZ-Link Sulfo-NHS-LC-Biotin (ThermoFisher Scientific) to biotinylate exposed membrane proteins. In parallel, RIPA extracts prepared from equivalent numbers of E98 cells and freed of Tris by repeated washing over Amicon Ultra K10 centrifugal filters (Merck Millipore, Billerica, Mass., USA) were treated similarly to biotinylate all cellular proteins. The reaction was quenched by washing cells or cytosolic proteins three times with 100 mM glycine/PBS and two times with PBS (using K10 columns in the case of protein lysates). Treated adherent cells were then subjected to lysis with RIPA buffer. Protein concentrations in all lysates were determined using the BCA protein concentration assay (ThermoFisher Scientific) according to standard procedures. MET was immunoprecipitated from 200 µg total protein in 200 µl using anti-MET (1:50, clone D1C2, CST) for 1 hour at 4° C. Immune complexes were captured by incubation for 30 min at 4° C. with 10 µl prot A agarose slurry (Roche Diagnostics, Basel, Switzerland), followed by centrifugation (14.000 rpm, 4 min) and three PBS washes. Immune complexes were solubilized by heating (5 min 95° C.) in 30 µl 2×SDS-PAGE sample buffer (0.2% SDS, 62.5 mM Tris-HCl pH 6.8, 10% glycerol and 0.2 µM DTT). Samples were subjected to 10% SDS-PAGE and western blotting as described above.

Results

E98 MET Protein is Auto-Activated in an HGF-Independent Fashion.

Figure 1B:
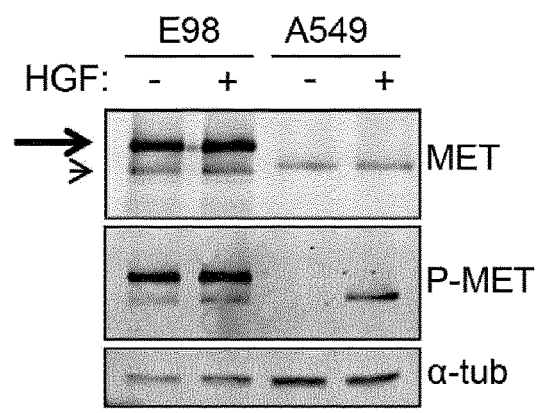
Figure 1C:
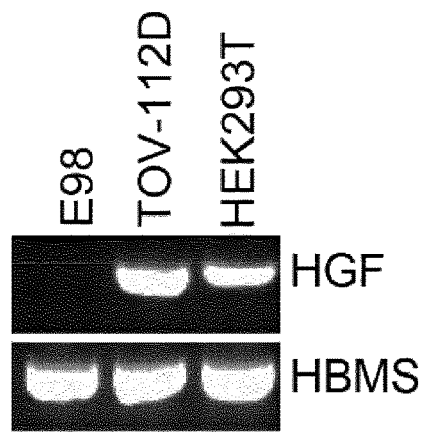

Our previous experiments have shown that MET in E98 xenografts is phosphorylated in tumor cells in a homogeneous fashion (FIG. 1A, see also (Navis et al., 2013)). In vitro, E98 cells also show high levels of phosphorylated MET when grown under serum-free conditions (FIG. 1B). HGF treatment did not further increase phosphorylation levels of MET, in contrast to A549 control cells in which HGF was required for MET activation. MET phosphorylation in E98 cells was not the result of endogenous HGF expression as revealed by RT-PCR analysis (FIG. 1C), while analysis of E98 xenograft RNA revealed the presence of mouse HGF only, as determined by Sanger sequencing (not shown). Since mouse HGF is not an activating ligand for human MET (Ohgaki and Kleihues, 2005; Zhang et al., 2005) we conclude that constitutive activation of MET in E98 cells and xenografts is not the result of an autocrine HGF-activation loop.

E98 Cells Express a Truncated Version of an Amplified MET Gene.

Figure 2A:
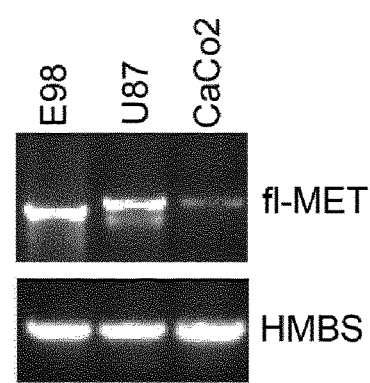
Figure 2C:
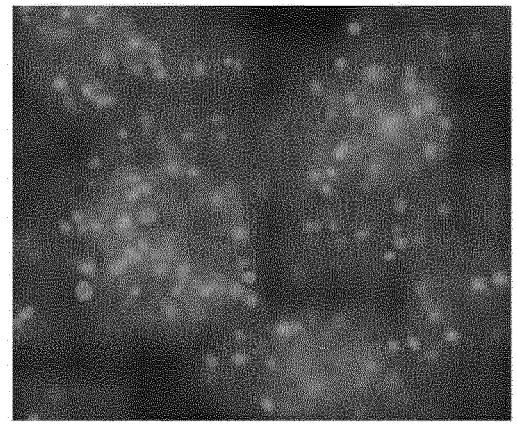
Figure 2D:
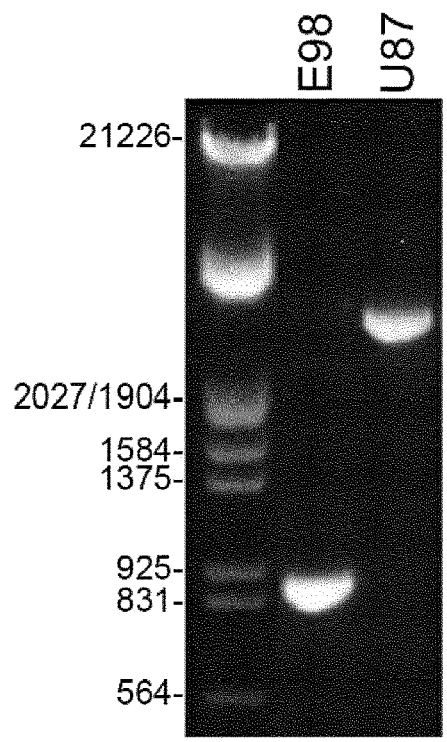
Figure 2B:
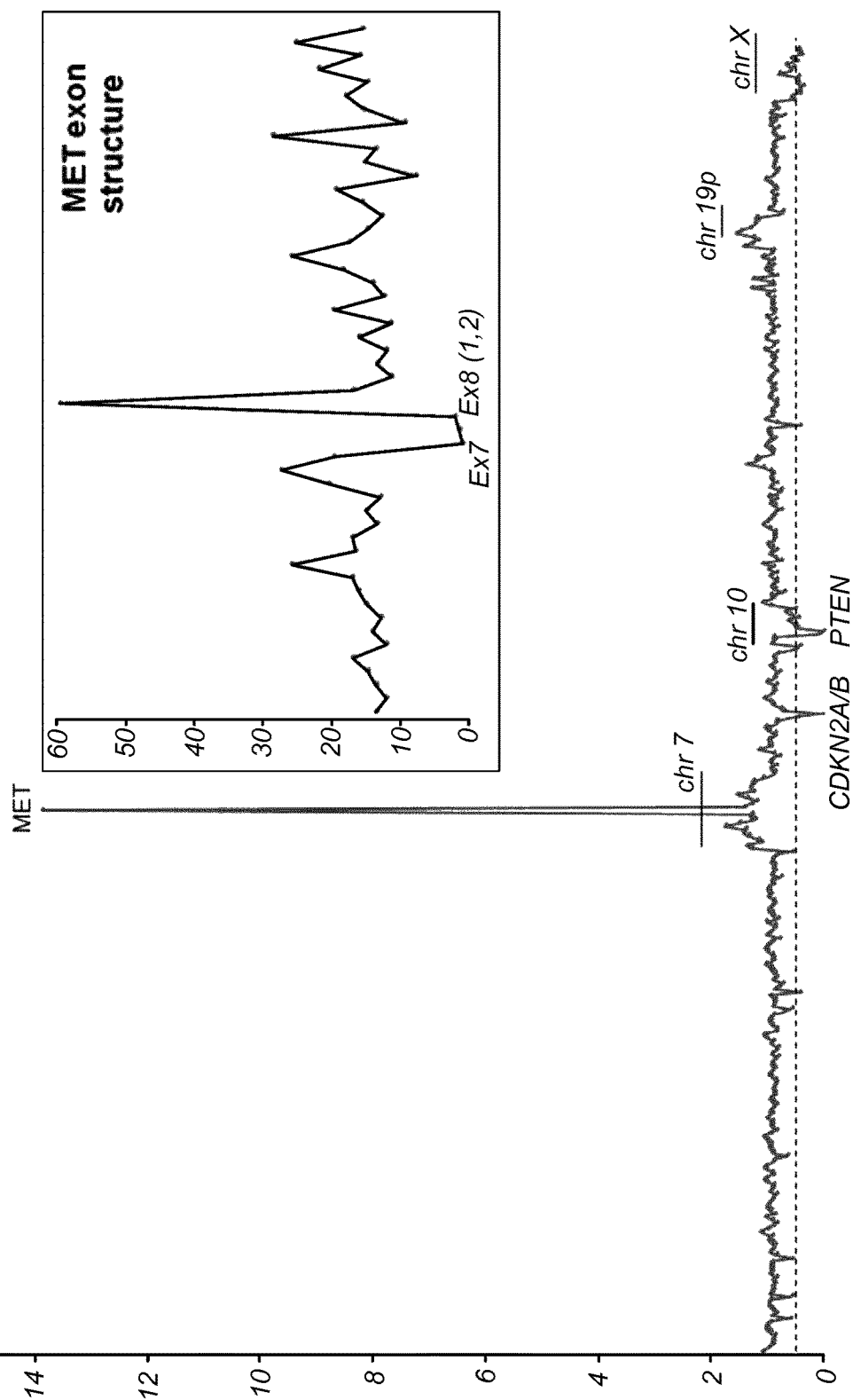
Figure 2E:
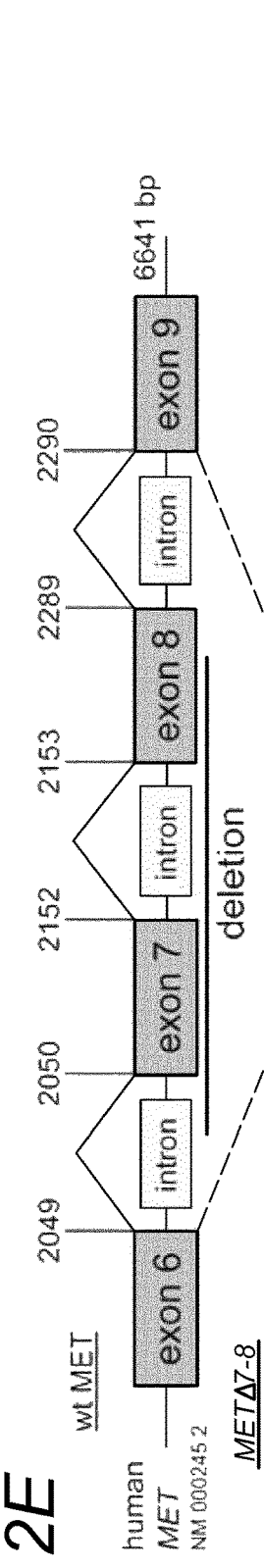

To examine the underlying mechanism of MET auto-activation in this model, we PCR-cloned MET cDNA from E98 cells, using primers flanking the open reading frame (ORF, NM_000245.2). The MET PCR product from E98 was 240 bp smaller than that from U87 and CaCo2 cDNA (FIG. 2A), and Sanger sequencing analysis revealed an in-frame deletion of nt 2050-2289 in the coding sequence, corresponding to exons 7 and 8. The same transcript was also found in E98 xenografts (not shown). Genomic analysis of E98 cells using semi-conductor sequencing revealed high copy MET amplification (FIG. 2B). Average amplification of MET was about 14-fold. FISH analysis using probes specific for MET and chromosome 7 centromere confirmed the amplification (FIG. 2C). Consistent with Sanger sequencing, amplicons in exon 7 and the first part of exon 8 were absent (see insert in FIG. 2B), suggesting that the lack of exons 7 and 8 results from a genomic rearrangement. (similar to the EGFR variant III (Gan et al., 2013)) instead of alternative splicing. PCR on genomic DNA using exon 6 and 9 specific primers resulted in amplification of a 910 bp fragment (predicted size from the wild-type allele, present in U87, is 3,014 bp, see FIG. 2D). Sequencing of this product revealed an intronic deletion of 2,114 bp (between position g. 116 395 653 located in intron 6, and 116 397 766, located in exon 8). This deletion results in an intact splice donor site from exon 6, juxtaposed to the exon 9 splice acceptor site, and explains the lack of exons 7 and 8 in the resulting mRNA (FIG. 2E). Of note, a wtMET allele could not be detected in E98 cells (FIG. 2D).

Figure 3A:
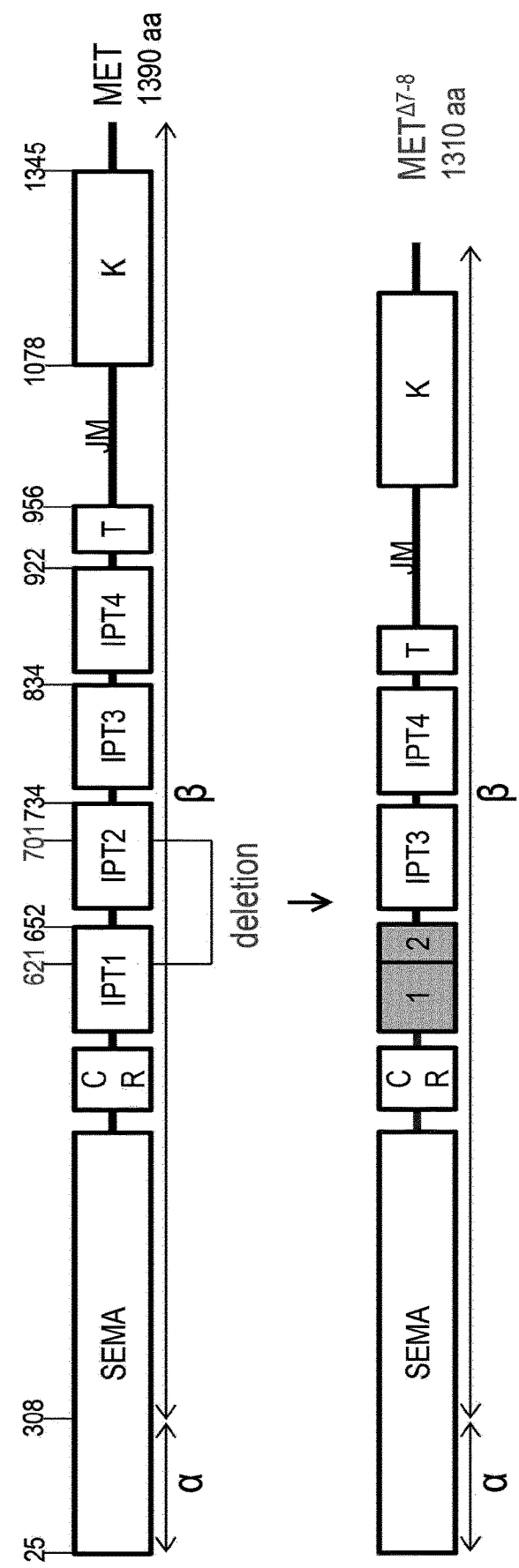
Figure 3B:
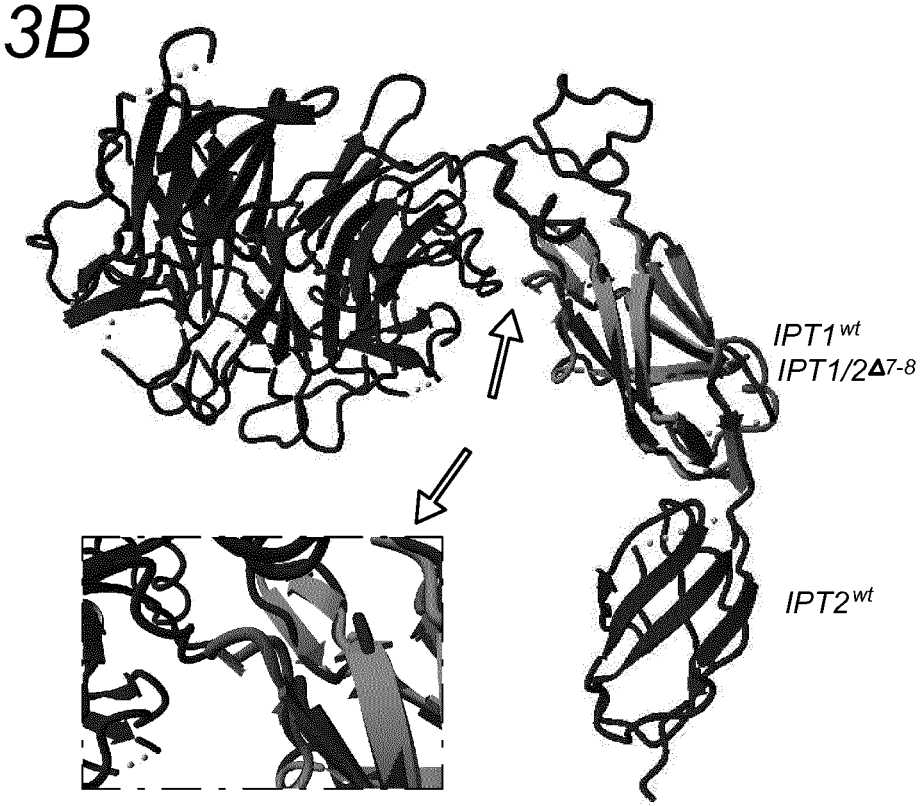

On the protein level, this rearrangement leads to loss of the C-terminus of IPT1 and the N-terminus of IPT2 (FIG. 3A). Yasara modeling, using X-ray crystallographic data of the MET ectodomain, predicts the formation of a novel IPT, composed of the remaining parts of IPT1 and 2. Interestingly, in the new IPT1/2 fusion a small stretch of 5 extra amino acids loops out towards the Sema domain (FIG. 3B).

METΔ7-8 is Aberrantly Processed

Figure 4A:
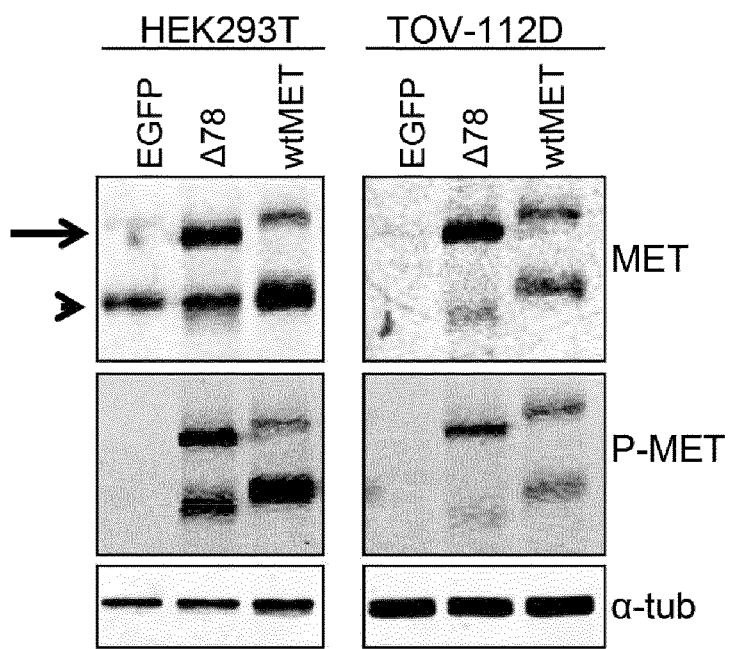

MET is synthesized as a 190 kDa precursor protein which is proteolytically cleaved by furin between residues 307 and 308, to yield an extracellular α-chain of approximately kDa, covalently linked via a disulfide bridge to the transmembrane β-chain. Reducing SDS-PAGE, followed by western blot analysis of E98 cell extracts showed that the majority of MET protein was in a 180 kDa phosphorylated form, corresponding to the uncleaved truncated preform (FIG. 1B, arrow). In contrast, in A549 cells the matured, cleaved MET protein was the predominant form (arrowhead in FIG. 1B). To investigate whether this was a specific feature of E98 cells, we analyzed the protein structure in cells after transfection with the full-length cDNAs encoding wtMET or METΔ7-8. In both HEK-293T and TOV-112D cells, wtMET was properly processed to an α- and β-chain, indicating that these cells are not defective in furin-mediated processing. In contrast, METΔ7-8 was predominantly present in the uncleaved preform in both cell types (FIG. 4A, arrow). Thus, improper MET cleavage is an intrinsic property of METΔ7-8. Overexpression studies in HEK-293T and TOV-112D cells resulted in phosphorylated Y1234/1235 residues in both wtMET and METΔ7-8 proteins (FIG. 4A, P-MET). Because both cell lines produce HGF (FIG. 1C) this may be a result of HGF-dependent autocrine activation.

Figure 4B:
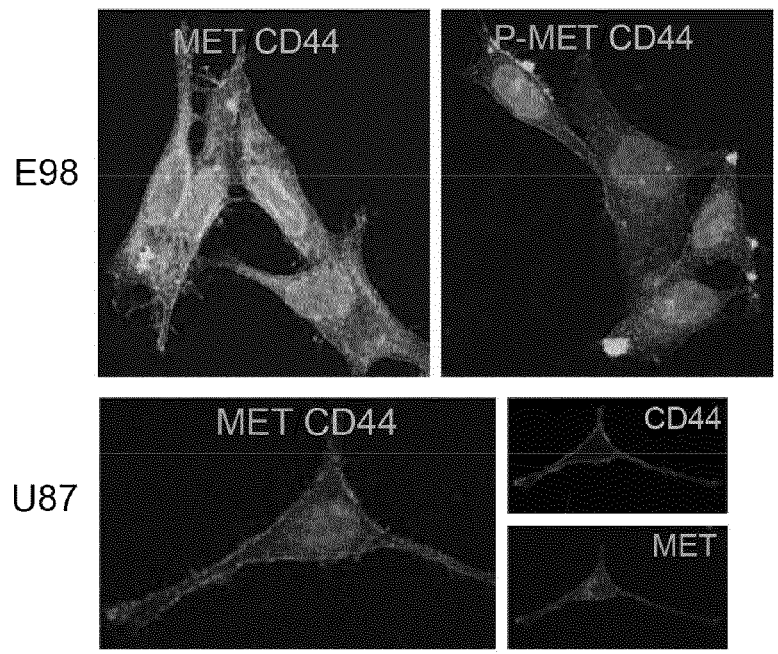
Figure 4C:
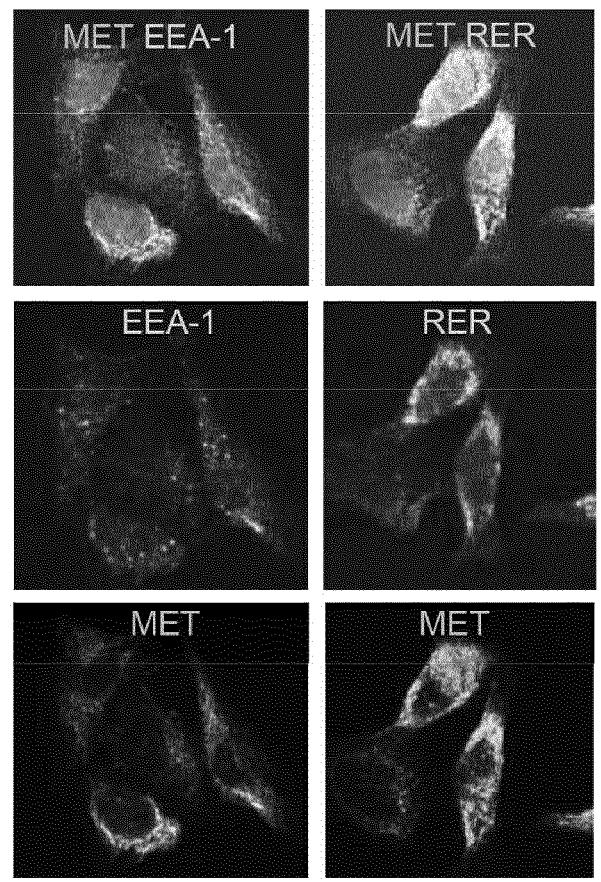

MET is cleaved by the endoprotease Furin, which is localized predominantly in the Trans Golgi Network, but also in vesicles and near the plasma membrane (Komada et al., 1993; Molloy et al., 1994; Schafer et al., 1995). To test whether the inefficient cleavage of METΔ7-8 in E98 cells is related to intracellular transport defects, we analyzed the subcellular localization of METΔ7-8 in detail via confocal microscopy. METΔ7-8 did not co-localize with the cell surface marker CD44 and was confined to the cytosol (FIG. 4B). In contrast, on U87 cells wtMET did co-localize with CD44. Additional intracellular staining in U87 cells reflects de novo synthesized material that is being processed for constitutive secretion. Immunostainings with the early endosome marker EEA-1 and the rough endoplasmic reticulum (RER) marker CLIMP-63 suggested that METΔ7-8 in E98 cells is predominantly retained in the RER (FIG. 4C).

Figure 4D:
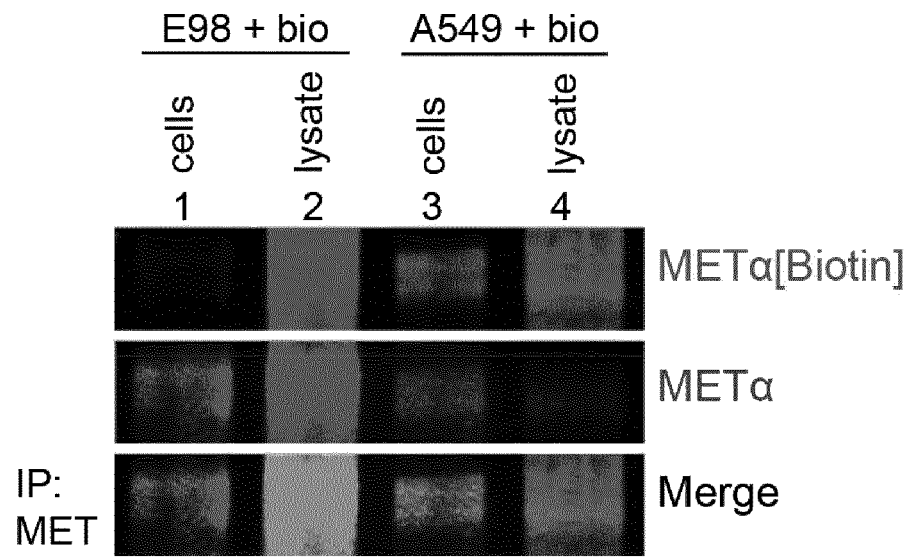

To confirm the absence of cell surface expression of METΔ7-8 on E98 cells, we labeled intact E98 cells or cell lysates with NHS-biotin and immunoprecipitated MET using specific antibodies, followed by SDS-PAGE/western blot and staining for biotin and MET. Whereas METs N-terminal α-chain was readily biotinylated in E98 cell lysates, only very little biotinylated MET was detected when intact cells were labeled (FIG. 4D, lane 1). In contrast, biotinylated MET was readily detected in A549 cells upon labeling of intact cells, as shown by the biotin-labeled α-chain (FIG. 4D, lane 3). Thus, these data confirm that METΔ7-8 is predominantly localized intracellularly and is poorly exposed on the cell surface of E98 cells.

Figure 4E:
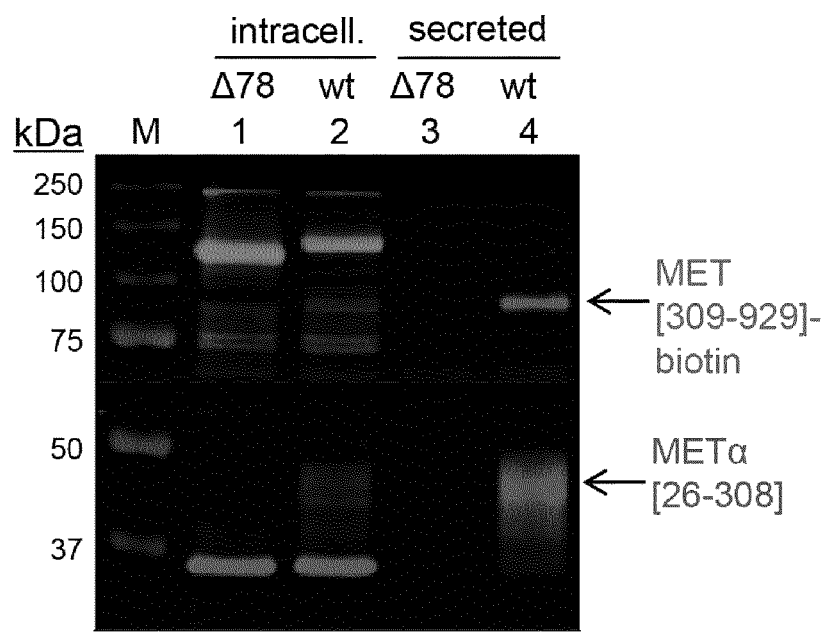

To further confirm a defect in intracellular trafficking of METΔ7-8 we analyzed secretion patterns of extracellular domains of wtMET or METΔ7-8 (ending with residue D929, numbering according to MET variant 2 (NP_000236.2), containing a C-terminal biotin tag. Whereas the extracellular domain of wtMET was properly processed and secreted into the culture medium (as illustrated by the presence of the 309-929 biotinyated extracellular β-chain and the MET25-308 α-chain, FIG. 4E, lane 4), no secreted MET products were found in medium of cells, transfected with the METΔ7-8 ectodomain (FIG. 4E, lane 3). Instead, all biotinylated MET products were located intracellularly (FIG. 4E, lane 1).

185 kDa METΔ7-8 is not Affected by Antagonistic Anti-MET Antibodies but is Inhibited by Cabozantinib It was previously reported that VHH G2, a recombinant single domain llama antibody against MET, results in low MET activation levels, while inhibiting the strong activation which is induced by HGF (Heukers et al., 2014). To test whether and how G2 affects phosphorylation of METΔ7-8, we treated serum-starved E98 cells with G2, either or not followed by HGF, using A549 cells as control. As shown in FIG. 5, HGF did not increase overall MET phosphorylation levels, although, interestingly, a slight activation was seen in the minority of processed β-fragment of MET. For G2 a similar effect was observed. Consistent with high overall MET phosphorylation levels in all samples, neither G2 nor HGF treatment resulted in altered levels of pAKT, a direct target of MET. In A549 cells G2 and HGF induced MET phosphorylation, which increased levels of pAKT. Thus, in contrast to A549 cells that express wtMET, E98 cells are not responsive to antibodies against or ligands of MET. However, both E98 and A549 cells responded well to the MET tyrosine kinase inhibitor cabozantinib (FIG. 5).

Prevalence of METΔ7-8

Figure 6A:
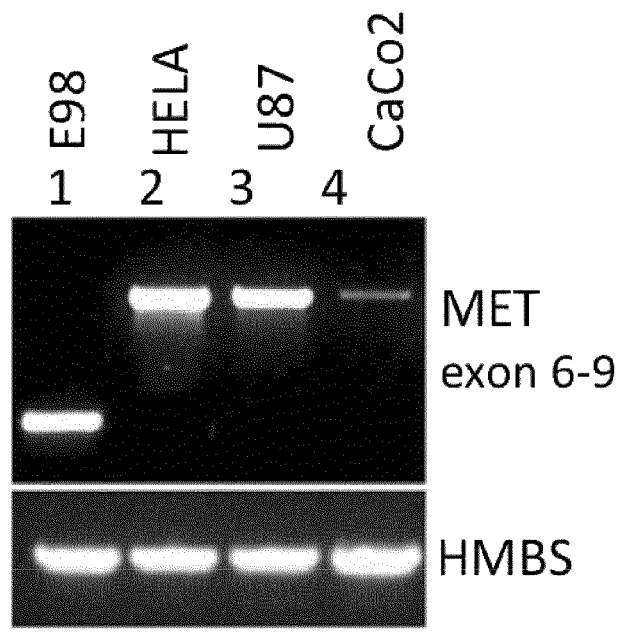
Figure 6B:
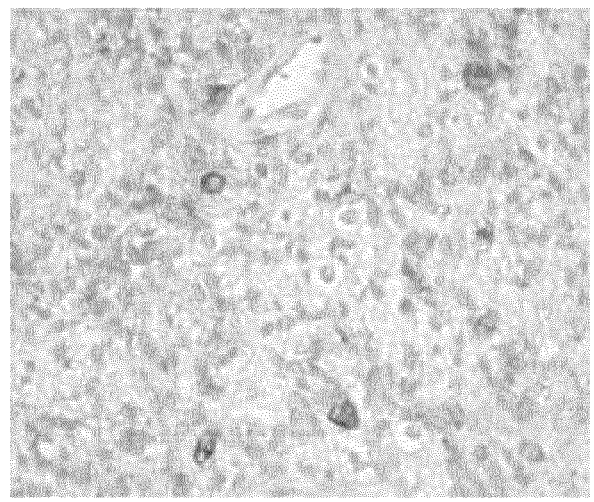
Figure 6C:
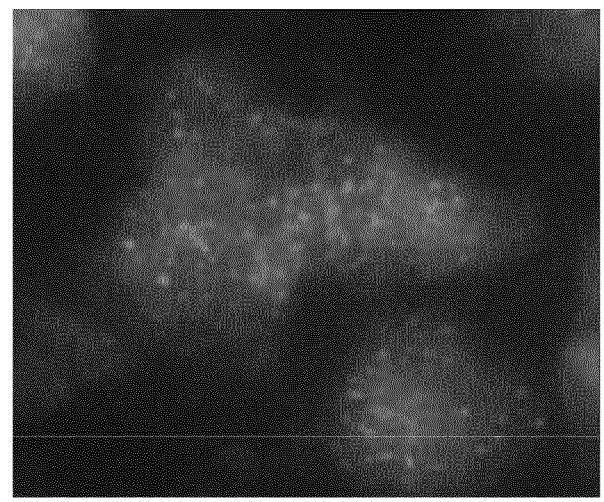

PCR with deletion-spanning primers revealed the sole presence of the deletion-specific 105 bp fragment in E98 cDNA, while a number of other cell lines presented with the wt 345 bp amplicon only (FIG. 6A). Since frozen material from the patient tumor that was used to generate E98 is unavailable, we could unfortunately not obtain genomic DNA and cDNA of sufficient quality to confirm the presence of the mutation in the originating tumor. We did however perform immunohistochemistry on formalin-fixed, paraffin-embedded tumor material from this patient and observed a highly heterogeneous staining for MET, with only a small percentage of strongly positive tumor cells, apparently with intracellular staining (FIG. 6B). Of note, such immunostainings cannot discriminate between wtMET and METΔ7-8. FISH analysis confirmed the presence of the MET amplification in the original tumor (FIG. 6C).

Figure 6D:
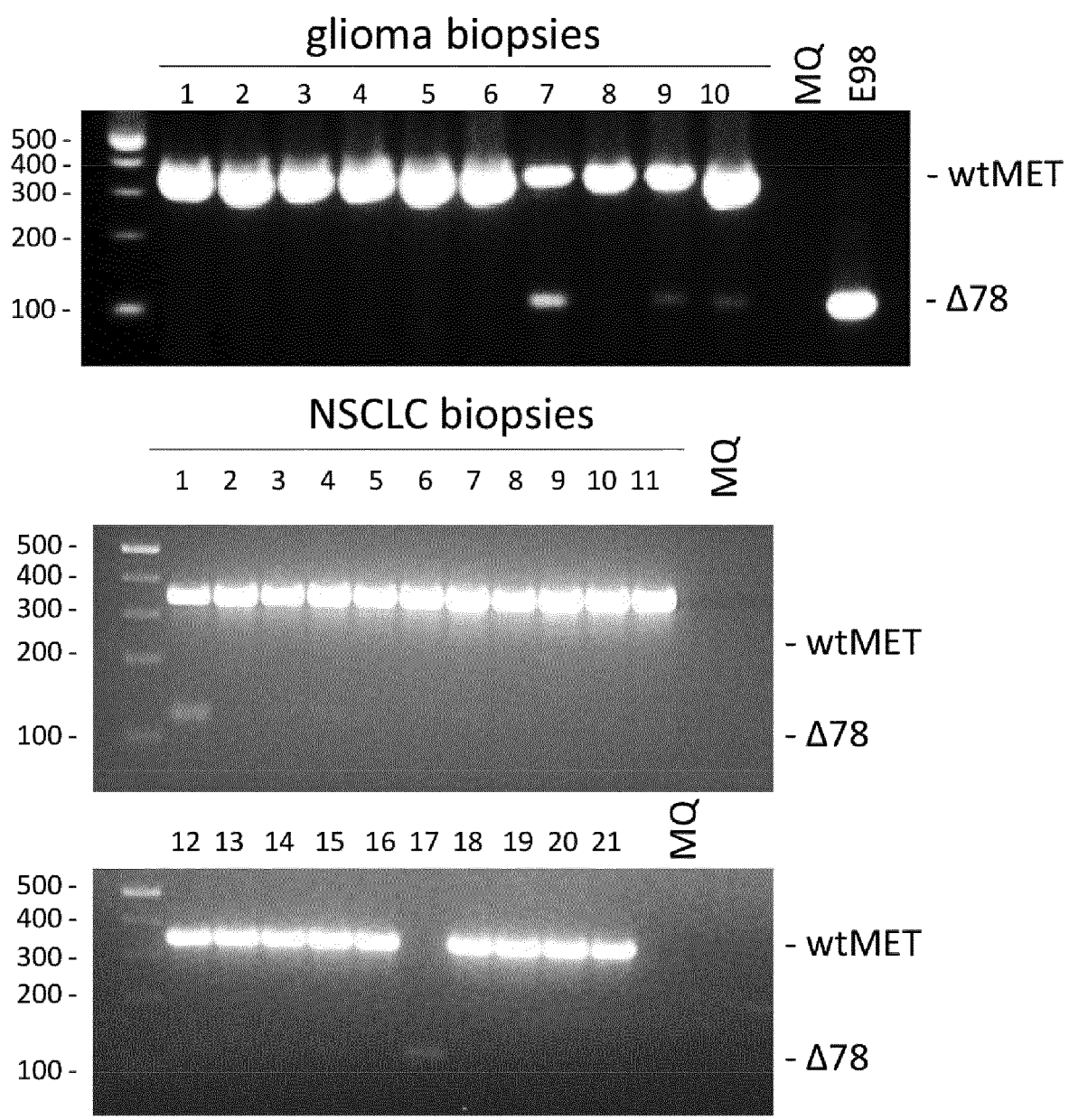

To investigate the prevalence of the METΔ7-8 mutation further, we performed the exon 6-9 PCR on cDNA, generated from a series of gliomas (n=102) and a number of other tumor types in which MET has been suggested to play an important role (castration resistant prostate carcinomas, n=43; Ewing sarcoma, n=21; rhabdomyosarcoma, n=22; NSCLC, n=21) (Humphrey et al., 1995; Knudsen et al., 2002). METΔ7-8 was found in 6 out of 102 gliomas, both grade III and IV (5.8%; 2 out of 5 anaplastic oligodendrogliomas, 2 out of 16 anaplastic astrocytomas and 2 out of 61 glioblastomas), and was not detected in the other tumor types tested, except for NSCLC (example in FIG. 6D and Table 2). Most tumors that contained the mutation were heterozygous, containing also the wild-type transcript, whereas in one sample of NSCLC only the mutated MET transcript could be detected (FIG. 6D). Sanger sequencing of the smaller PCR products of one patient with glioma and NSCLC confirmed the deletion of exons 7 and 8 (not shown). Of note, due to the lack of high quality genomic DNA from these clinical samples we could not discriminate in these samples whether METΔ7-8 resulted from a mutation or from exon skipping or alternative splicing, such as suggested for MET variants lacking exon 10 or 14 (Ma et al., 2003).

Discussion

A major problem in glioma treatment is diffuse growth in the neuropil, and it has been suggested that the MET oncogene is causally involved in this phenotype in subsets of tumors. The MET signal transduction pathway is also increasingly recognized as a rescue pathway, generating resistance to EGFR-targeted therapies (Corso and Giordano, 2013). We previously reported that MET is crucially implicated in proliferation, survival and migration of E98 glioma cells in vitro and showed that treatment with the MET tyrosine kinase inhibitor cabozantinib prolongs survival of mice carrying orthotopic E98 xenografts (Navis et al., 2013). Based on the observation that the pattern of MET phosphorylation in E98 xenografts was remarkably homogeneous in the absence of its ligand HGF, we analyzed the MET product in E98 cells in more detail and found that the protein is expressed as a truncated product, which lacks effective furin cleavage and is predominantly retained intracellularly in its active, phosphorylated form. The truncation generates a novel IPT domain consisting of a fusion between the carboxyterminus of IPT1 and the amino terminus of IPT2. Modeling of the novel fusion IPT domain suggests that it adopts a similar structure as the IPT domains in wild type MET, although a small stretch of extra amino acid residues is accommodated in a loop, extending towards the Sema domain. Since this loop approaches the furin-cleavage site in the Sema domain, it may directly impact on furin cleavage, but this requires further investigation.

The METΔ7-8 mutant resembles the auto-active EGFRvIII variant. This variant results from a genetic deletion of exons 2-7 and its activation is also independent of the ligands EGF or TNFα. Like the EGFRvIII mutation (Gan et al., 2013), the METΔ7-8 alteration appears to be restricted to only few cancer types, as we detected it in glioma and NSCLC. The mutation was detected in grade III gliomas of both oligodendroglial and astrocytic origin and GBMs.

Interestingly, we did not detect a wtMET transcript in E98 cells, in contrast to the clinical gliomas which were analyzed in this study and which all showed abundant wtMET, also in METΔ7-8 tumors. Only one NSCLC sample also showed exclusive METΔ7-8 expression. We formally cannot exclude that the wild type MET amplicons in our PCR derive from 'contaminating' non-neoplastic stromal cells in the tumor biopsies. There may however be another explanation for the relatively low levels of METΔ7-8 in clinical tumors: in the patient tumor from which the E98 model was generated, a low percentage of MET-expressing tumor cells was detected, although it is impossible to determine whether these cells carry the METΔ7-8 mutation because the antibodies used do not discriminate between MET and METΔ7-8. It is tempting to speculate that during the generation of the E98 model, a small subset of MET-mutated tumor cells in the primary tumor experienced a growth advantage, ultimately resulting in clonal outgrowth and xenografts. This scenario fits with the notion that clinical tumors not only show inter—but also intratumoral heterogeneity (Sottoriva et al., 2013), and derived preclinical tumor models may only be representative for the most malignant population of tumor cells. Our finding may have important consequences for therapy. MET is increasingly recognized as an important target in multiple tumor types, and therapeutic antibodies against HGF or the HGF binding site on MET have been developed. Since HGF is not involved in METΔ7-8 activation and METΔ7-8 is retained intracellularly, MET-mutated cells will not be responsive to these therapies. Indeed we were able to show that E98 cells do not respond to the anti-MET VHH G2. Selection of MET-mutated cells in tumors that initially respond to antibody-based MET-directed treatment is expected to result in recurrence of treatment-resistant clones. In this respect, it will be important in future studies to assess the occurrence of the Δ7-8 mutation in paired samples of primary and recurrent tumors after MET-antibody-based therapies. With this in mind, the use of specific tyrosine kinase inhibitors of MET may have preference over antibody-based therapy, since METΔ7-8 is sensitive to these inhibitors (Navis et al., 2013). Such inhibitors have already shown to improve overall survival of patients with non-small cell lung carcinoma with MET amplification and renal papillary carcinoma with MET mutations (Choueiri et al., 2013; Ou et al., 2011). A recent phase II study with the antibody MetMab for lung cancer failed to meet the primary end point of prolonged survival (Spigel et al., 2013). A study of MET mutations and intracellular localization patterns in this patient group may be highly informative for future therapeutic directions (Hirsch et al., 2014).

The Δ7-8 alteration leads to a reduction in furin-mediated cleavage of the MET precursor. Interestingly, the colorectal adenocarcinoma cell line Lovo lacks furin protease and consequently cannot properly process MET (Mark et al., 1992). In this cell line, the unprocessed preform is still expressed on the cell surface, binds HGF and is capable of signaling. Thus, defective processing alone does not explain intracellular retention of METΔ7-8 and we therefore hypothesize that the novel IPT1-2 fusion domain in. METΔ7-8 is involved in defective furin cleavage, intracellular retention of the uncleaved perform and auto-activation of the uncleaved preform.

Recently, effects of various activating mutations in the MET TK domain have been analyzed in detail. Interestingly, these mutants are expressed on the cell surface but are subject to increased rates of turnover, resulting in accumulation in early endosomes where they can still signal (Joffre et al., 2011). METΔ7-8 did not accumulate in early endosomes, suggesting that the underlying mechanism of intracellular retention is different (Mu et al., 1995). Our confocal microscopy and biotinylation experiments strongly suggest that only the very small fraction of METΔ7-8 that is cleaved reaches the cell membrane, but this fraction is insignificant with respect to the auto-active component in the cytosol.

Deletions in the extracellular domains of tyrosine kinase receptors are not uncommon in glioma, a prime example being EGFRvIII. The vIII mutation, concomitant with EGFR amplification, occurs in 25-64% of all GBMs (Aldape et al., 2004; Biemat et al., 2004; Feldkamp et al., 1999; Saikali et al., 2007; Viana-Pereira et al., 2008). Furthermore, 40% of the GBMs with amplified PDGFRA contain an in-frame deletion in the ectodomain, leading to constitutive activation of the TK domain (Kumabe et al., 1992; Ozawa et al., 2010). Recently, also in pediatric high grade gliomas ligand-independent and tumorigenic in-frame PDGFRA deletion variants have been found (Kumabe et al., 1992; Paugh et al., 2013; Rand et al., 2005; Verhaak et al., 2010). Data on the subcellular localization of mutated oncoreceptors is frequently lacking, and our data call for in-depth analysis of the cellular localization of receptors that are considered targetable. Interestingly, activating mutations in the RON tyrosine kinase receptor have been identified which resemble the METΔ7-8 mutation in that it also involves the first IPT domain (Ma et al., 2010). Of note, these alterations do not lead to a loss of expression at the cell surface.

In conclusion, we describe a highly active, non-ligand dependent mutant of MET in a subset of patients with glioma and NSCLC, which is not exposed on the cell surface and is predicted to be non-targetable with therapeutic antibodies against MET and/or HGF.

TABLE 2

METΔ7-8 expression in glioma; sarcoma and CRPCs
The incidence of METΔ7-8 in different subtypes and malignancy grades of diffuse glioma, sarcomas, and castration resistant prostate carcinomas (CRPC). Abbreviations: O-II, oligodendroglioma WHO grade II; O-III, oligodendroglioma (WHO grade III); A-II, astrocytoma WHO grade II; A-III, anaplastic astrocytoma, WHO grade III; GBM, glioblastoma.

| Tumor type | Δ7/8 occurance |
|---|---|
| Glioma | 6/102 (5.8%) |
| O-II | 0/3 |
| A-II | 0/7 |
| OA-II | 0/5 |
| O-III | 2/5 (40%) |
| A-III | 2/16 (12.5%) |
| OA-III | 0/5 |
| GBM | 2/61 (1.64%) |
| Sarcoma | 0/25 |
| Ewing tumor | 0/5 |
| Cell line | 0/3 |
| Rhabdo tumor | 0/15 |
| Cell line | 0/2 |
| CRPC | 0/43 |
| NSCLC | 3/21 |

Example 2. A Robust Discriminative PCR for the Detection of the Novel MET Mutation (METΔ7-8) Resulting in an Auto-Active Intracellular Protein.

To develop a robust, discriminative PCR, primer METFW2033junct6_9 was designed in which the last six nucleotides are specific to exon 9 and consequently do not hybridize to exon 7, whereas the remaining nucleotides hybridize to exon 6. This means that this primer specifically recognizes METdelta7/8 cDNA, but not wild-type MET cDNA. The combination of METFW2033junct6_9 and METrev2393 results in a product of 120 bp when the mutation is present that results in a MET lacking exon 7 and 8; the combination of METFW2033junct6_9 and METrev2561 results in a product of 268 bp when the mutation is present that results in a MET lacking exon 7 and 8. Wild-type MET results in no PCR product.

FIG. 7 demonstrates that this primer, in combination with either MET2393rev or MET2561rev (both located in exon 9) indeed recognizes METdelta7/8 and not wild-type MET; this is demonstrated at three different annealing temperatures. Lanes 5 comprises a mixture of templates; METd7/8: wild-type MET cDNA (1:99) and shows that under the conditions used, only the METd7/8 is amplified in absence of wild-type MET. PCR was carried out using standard conditions on 1 ng of template DNA/reaction. The cycle protocol was: an initial denature step of 30" at 94° C., followed by 25 cycles of 15" at 94° C.; 30" at 58° C., 60° C. or 62° C.; 30" at 72° C., followed by a final elongation step of 2' at 72° C.

The gel lanes in FIG. 7 correspond to the following PCR reactions at three different annealing temperatures:

| lane | template | forward primer | reverse primer |
|---|---|---|---|
| 1: | 1 ng METdelta7/8 | x MET2033FWjunct6_9 | x MET2393R |
| 2: | 1 ng METwt | x MET2033FWjunct6_9 | x MET2393R |
| 3: | 1 ng METdelta7/8 | x MET2033FWjunct6_9 | x MET2561R |
| 4: | 1 ng METwt | x MET2033FWjunct6_9 | x MET2561R |
| 5: | 10 pg METd78 + 1 ng METwt | x MET2033FWjunct6_9 | x MET2393R |
| 6: | No template | x MET2033FWjunct6_9 | x MET2393R |
| 7: | No template | x MET2033FWjunct6_9 | x MET2561R |

REFERENCE LIST

Aldape, K. D., Ballman, K., Furth, A., Buckner, J. C., Giannini, C., Burger, P. C., Scheithauer, B. W., Jenkins, R. B., and James, C. D. (2004). Immunohistochemical detection of EGFRvIII in high malignancy grade astrocytomas and evaluation of prognostic significance. Journal of neuropathology and experimental neurology 63, 700-707.

Asaoka, Y., Tada, M., Ikenoue, T., Seto, M., Imai, M., Miyabayashi, K., Yamamoto, K., Yamamoto, S., Kudo, Y., Mohri, D., et al. (2010). Gastric cancer cell line Hs746T harbors a splice site mutation of c-Met causing juxtamembrane domain deletion. Biochemical and biophysical research communications 394, 1042-1046.

Biernat, W., Huang, H., Yokoo, H., Kleihues, P., and Ohgaki, H. (2004). Predominant expression of mutant EGFR (EGFRvIII) is rare in primary glioblastomas. Brain pathology 14, 131-136.

Bladt, F., Riethmacher, D., Isenmann, S., Aguzzi, A., and Birchmeier, C. (1995). Essential role for the c-met receptor in the migration of myogenic precursor cells into the limb bud. Nature 376, 768-771.

Borowiak, M., Garratt, A. N., Wustefeld, T., Strehle, M., Trautwein, C., and Birchmeier, C. (2004). Met provides essential signals for liver regeneration. Proceedings of the National Academy of Sciences of the United States of America 101, 10608-10613.

Cancer Genome Atlas Research, N. (2008). Comprehensive genomic characterization defines human glioblastoma genes and core pathways. Nature 455, 1061-1068.

Caretti, V., Zondervan, I., Meijer, D. H., Idema, S., Vos, W., Hamans, B., Bugiani, M., Hulleman, E., Wesseling, P., Vandertop, W. P., et al. (2011). Monitoring of tumor growth and post-irradiation recurrence in a diffuse intrinsic pontine glioma mouse model. Brain Pathol 21, 441-451.

Chan, A. M., King, H. W., Deakin, E. A., Tempest, P. R, Hilkens, J., Kroezen, V., Edwards, D. R., Wills, A. J., Brookes, P., and Cooper, C. S. (1988). Characterization of the mouse met proto-oncogene. Oncogene 2, 593-599.

Chmielowiec, J., Borowiak, M., Morkel, M., Stradal, T., Munz, B., Werner, S., Wehland, J.; Birchmeier, C., and Birchmeier, W: (2007). c-Met is essential for wound healing in the skin. The Journal of cell biology 177, 151-162.

Choueiri, T. K., Vaishampayan, U., Rosenberg, J. E., Logan, T. F., Harzstark, A. L., Bukowski, R. M., Rini, B. I., Srinivas, S., Stein, M. N., Adams, L. M., et al. (2013). Phase II and biomarker study of the dual MET/VEGFR2 inhibitor foretinib in patients with papillary renal cell carcinoma. Journal of clinical oncology: official journal of the American Society of Clinical Oncology 31, 181-186.

Chretien, S., Dubart, A., Beaupain, D., Raich, N., Grandchamp, B., Rosa, J., Goossens, M., and Romeo, P. H. (1988). Alternative transcription and splicing of the human porphobilinogen deaminase gene result either in tissue-specific or in housekeeping expression. Proceedings of the National Academy of Sciences of the United States of America 85, 6-10.

Claes, A., Schuuring, J., Boots-Sprenger, S., Hendriks-Cornelissen, S., Dekkers, M., van der Kogel, A. J., Leenders, W. P., Wesseling, P., and Jeuken, J. W. (2008). Phenotypic and genotypic characterization of orthotopic human glioma models and its relevance for the study of anti-glioma therapy. Brain Pathol 18, 423-433.

Corso, S., and Giordano, S. (2013). Cell-autonomous and non-cell-autonomous mechanisms of HGF/MET-driven resistance to targeted therapies: from basic research to a clinical perspective. Cancer discovery 3, 978-992.

Feldkamp, M. M., Lala, P., Lau, N., Roncari, L., and Guha, A. (1999). Expression of activated epidermal growth factor receptors, Ras-guanosine triphosphate, and mitogen-activated protein kinase in human glioblastoma multiforme specimens. Neurosurgery 45, 1442-1453.

Ferracini, R., Longati, P., Naldini, L., Vigna, E., and Comoglio, P. M. (1991). Identification of the major autophosphorylation site of the Met/hepatocyte growth factor receptor tyrosine kinase. The Journal of biological chemistry 266, 19558-19564.

Gan, H. K., Cvrljevic, A. N., and Johns, T. G. (2013). The epidermal growth factor receptor variant III (EGFRvIII): where wild things are altered. The FEBS journal 280, 5350-5370.

Gherardi, E., Birchmeier, W., Birchmeier, C., and Vande Woude, G. (2012). Targeting MET in cancer: rationale and progress. Nature reviews Cancer 12, 89-103.

Gherardi, E., Youles, M. E., Miguel, R. N., Blundell, T. L., Iamele, L., Gough, J., Bandyopadhyay, A., Hartmann, G., and Butler, P. J. (2003). Functional map and domain structure of MET, the product of the c-met protooncogene and receptor for hepatocyte growth factor/scatter factor. Proceedings of the National Academy of Sciences of the United States of America 100, 12039-12044.

Goździk-Spychalska J, Szyszka-Barth K, Spychalski L, Ramlau K, Wójtowicz J, Batura-Gabryel H and Ramlau R. (2014). c-MET Inhibitors in the Treatment of Lung Cancer. Curr Treat Options Oncol. 4, 670-682.

Hammond, D. E., Urbe, S., Vande Woude, G. F., and Clague, M. J. (2001). Down-regulation of MET, the receptor for hepatocyte growth factor. Oncogene 20, 2761-2770.

Heukers, R., Altintas, I., Raghoenath, S., De Zan, E., Pepermans, R., Roovers, R. C., Haselberg, R., Hennink, W. E., Schiffelers, R. M., Kok, R. J., and van Bergen en Henegouwen, P. M. (2014). Targeting hepatocyte growth factor receptor (Met) positive tumor cells using internalizing nanobody-decorated albumin nanoparticles. Biomaterials 35, 601-610.

Hirsch, F. R., Bunn, P. A., Jr., and Herbst, R S. (2014). "Companion diagnostics": has their time come and gone? Clin Cancer Res 20, 4422-4424.

Huh, C. G., Factor, V. M., Sanchez, A., Uchida, K., Conner, E. A., and Thorgeirsson, S. S. (2004). Hepatocyte growth factor/c-met signaling pathway is required for efficient liver regeneration and repair. Proceedings of the National Academy of Sciences of the United States of America 101, 4477-4482.

Humphrey, P. A., Zhu, X., Zarnegar, R., Swanson, P. E., Ratliff, T. L., Vollmer, R. T., and Day, M. L. (1995). Hepatocyte growth factor and its receptor (c-MET) in prostatic carcinoma. The American journal of pathology 147, 386-396.

Jeffers, M., Taylor, G. A., Weidner, K. M., Omura, S., and Vande Woude, G. F. (1997). Degradation of the Met tyrosine kinase receptor by the ubiquitin-proteasome pathway. Molecular and cellular biology 17, 799-808.

Joffre, C., Barrow, R., Menard, L., Calleja, V., Hart, I. R., and Kermorgant, S. (2011). A direct role for Met endocytosis in tumorigenesis. Nature cell biology 13, 827-837.

Knudsen, B. S., Gmyrek, G. A., Inra, J., Scherr, D. S., Vaughan, E. D., Nanus, D. M., Kattan, M. W., Gerald, W. L., and Vande Woude, G. F. (2002). High expression of the Met receptor in prostate cancer metastasis to bone. Urology 60, 1113-1117.

Komada, M., Hatsuzawa, K., Shibamoto, S., Ito, F., Nakayama, K., and Kitamura, N. (1993). Proteolytic processing of the hepatocyte growth factor/scatter factor receptor by furin. FEBS letters 328, 25-29.

Kong-Beltran, M., Seshagiri, S., Zha, J., Zhu, W., Bhawe, K., Mendoza, N., Holcomb, T., Pujara, K., Stinson, J., Fu, L., et al. (2006). Somatic mutations lead to an oncogenic deletion of met in lung cancer. Cancer research 66, 283-289.

Krieger, E., Koraimann, G., and Vriend, G. (2002). Increasing the precision of comparative models with YASARA NOVA—a self-parameterizing force field. Proteins 47, 393-402.

Kumabe, T., Sohma, Y., Kayama, T., Yoshimoto, T., and Yamamoto, T. (0.1992). Overexpression and amplification of alpha-PDGF receptor gene lacking exons coding for a portion of the extracellular region in a malignant glioma. The Tohoku journal of experimental medicine 168, 265-269.

Lai, A. Z., Abella, J. V., and Park, M. (2009). Crosstalk in Met receptor oncogenesis. Trends in cell biology 19, 542-551.

Lee, C. C., and Yamada, K. M. (1994). Identification of a novel type of alternative splicing of a tyrosine kinase receptor. Juxtamembrane deletion of the c-met protein kinase C serine phosphorylation regulatory site. The Journal of biological chemistry 269, 19457-19461.

Liu, Y., Tolbert, E. M., Sun, A. M., and Dworkin, L. D. (1996). Primary structure of rat HGF receptor and induced expression in glomerular mesangial cells. The American journal of physiology 271, F679-688, Longati, P., Bardelli, A., Ponzetto, C., Naldini, L., and Comoglio, P. M. (1994). Tyrosines 1234-1235 are critical for activation of the tyrosine kinase encoded by the MET proto-oncogene (HGF receptor). Oncogene 9, 49-57.

Lu, K. V., Chang, J. P., Parachoniak, C. A., Pandika, M. M., Aghi, M. K., Meyronet, D., Isachenko, N., Fouse, S. D., Phillips, J. J., Cheresh, D. A., et al. (2012). VEGF Inhibits Tumor Cell Invasion and. Mesenchymal Transition through a MET/VEGFR2 Complex. Cancer Cell 22, 21-35.

Ma, P. C., Jagadeeswaran, R., Jagadeesh, S., Tretiakova, M. S., Nallasura, V., Fox, E. A., Hansen, M., Schaefer, E., Naoki, K., Lader, A., et al. (2005). Functional expression and mutations of c-Met and its therapeutic inhibition with SU11274 and small interfering RNA in non-small cell lung cancer. Cancer research 65, 1479-1488.

Ma, P. C., Kijima, T., Maulik, G., Fox, E. A., Sattler, M., Griffin, J. D., Johnson, B. E., and Salgia, R. (2003). c-MET mutational analysis in small cell lung cancer: novel juxtamembrane domain mutations regulating cytoskeletal functions. Cancer Res 63, 6272-6281.

Ma, P. C., Tretiakova, M. S., MacKinnon, A. C., Ramnath, N., Johnson, C., Dietrich, S., Seiwert, T., Christensen, J. G., Jagadeeswaran, R., Krausz, T., et al. (2008). Expression and mutational analysis of MET in human solid cancers. Genes Chromosomes Cancer 47, 1025-1037.

Ma, Q., Zhang, K., Guin, S., Zhou, Y. Q., and Wang, M. H. (2010). Deletion or insertion in the first immunoglobulin-plexin-transcription (IPT) domain differentially regulates expression and tumorigenic activities of RON receptor Tyrosine Kinase. Molecular cancer 9, 307.

Mark, M. R., Lokker, N. A., Zioncheck, T. F., Luis, E. A., and Godowski, P. J. (1992). Expression and characterization of hepatocyte growth factor receptor-IgG fusion proteins. Effects of mutations in the potential proteolytic cleavage site on processing and ligand binding. The Journal of biological chemistry 267, 26166-26171.

Molloy, S. S., Thomas, L., VanSlyke, J. K., Stenberg, P. E., and Thomas, G. (1994). Intracellular trafficking and activation of the furin proprotein convertase: localization to the TGN and recycling from the cell surface. The EMBO journal 13, 18-33.

Mu, F. T., Callaghan, J. M., Steele-Mortimer, O., Stenmark, H., Parton, R. G., Campbell, P. L., McCluskey, J., Yeo, J. P., Tock, E. P., and Toh, B. H. (1995). EEA1, an early endosome-associated protein. EEA1 is a conserved alpha-helical peripheral membrane protein flanked by cysteine "fingers" and contains a calmodulin-binding IQ motif. The Journal of biological chemistry 270, 13503-13511.

Navis, A. C., Bourgonje, A., Wesseling, P., Wright, A., Hendriks, W., Verrijp, K., van der Laak, J. A., Heerschap, A., and Leenders, W. P. (2013). Effects of dual targeting of tumor cells and stroma in human glioblastoma xenografts with a tyrosine kinase inhibitor against c-MET and VEGFR2. PLoS One 8, e58262.

Navis, A. C., Hamans, B. C., Claes, A., Heerschap, A., Jeuken, J. W., Wesseling, P., and Leenders, W. P. (2011). Effects of targeting the VEGF and PDGF pathways in diffuse orthotopic glioma models. J Pathol 223, 626-634.

Ohgaki, H., and Kleihues, P. (2005). Population-based studies on incidence, survival rates, and genetic alterations in astrocytic and oligodendroglial gliomas. J Neuropathol Exp Neurol 64, 479-489.

Onozato, R., Kosaka, T., Kuwano, H., Sekido, Y., Yatabe, Y., and Mitsudomi, T. (2009). Activation of MET by gene amplification or by splice mutations deleting the juxtamembrane domain in primary resected lung cancers. Journal of thoracic oncology: official publication of the International Association for the Study of Lung Cancer 4, 5-11.

Ou, S. H., Kwak, E. L., Siwak-Tapp, C., Dy, J., Bergethon, K., Clark, J. W., Camidge, D. R, Solomon, B. J., Maki, R. G., Bang, Y. J., et al. (2011). Activity of crizotinib (PF02341066), a dual mesenchymal-epithelial transition (MET) and anaplastic lymphoma kinase (ALK) inhibitor, in a non-small cell lung cancer patient with de novo MET amplification. Journal of thoracic oncology: official publication of the International Association for the Study of Lung Cancer 6, 942-946.

Ozawa, T., Brennan, C. W., Wang, L., Squatrito, M., Sasayama, T., Nakada, M., Huse, J. T., Pedraza, A., Utsuki, S., Yasui, Y., et al. (2010). PDGFRA gene rearrangements are frequent genetic events in PDGFRA-amplified glioblastomas. Genes Dev 24, 2205-2218.

Park, M., Dean, M., Kaul, K., Braun, M. J., Gonda, M. A., and Vande Woude, G. (1987). Sequence of MET proto-oncogene cDNA has features characteristic of the tyrosine kinase family of growth-factor receptors. Proceedings of the National Academy of Sciences of the United States of America 84, 6379-6383.

Paugh, B. S., Zhu, X., Qu, C., Endersby, R., Diaz, A. K., Zhang, J., Bax, D. A., Carvalho, D., Reis, R. M., Onar-Thomas, A., et al. (2013). Novel oncogenic PDGFRA mutations in pediatric high-grade gliomas. Cancer Res 73, 6219-6229.

Peschard, P., Fournier, T. M., Lamorte, L., Naujokas, M. A., Band, H., Langdon, W. Y., and Park, M. (2001). Mutation of the c-Cbl TKB domain binding site on the Met receptor tyrosine kinase converts it into a transforming protein. Molecular cell 8, 995-1004.

Petrelli, A., Gilestro, G. F., Lanzardo, S., Comoglio, P. M., Migone, N., and Giordano, S. (2002). The endophilin-CIN85-Cbl complex mediates ligand-dependent down-regulation of c-Met. Nature 416, 187-190.

Ponzetto, C., Bardelli, A., Zhen, Z., Maina, F., dalla Zonca, P., Giordano, S., Graziani, A., Panayotou, G., and Comoglio, P. M. (1994). A multifunctional docking site mediates signaling and transformation by the hepatocyte growth factor/scatter factor receptor family. Cell 77, 261-271.

Rand, V., Huang, J., Stockwell, T., Ferriera, S., Buzko, O., Levy, S., Busam, D., Li, K., Edwards, J. B., Eberhart, C., et al. (2005). Sequence survey of receptor tyrosine kinases reveals mutations in glioblastomas. Proceedings of the National Academy of Sciences of the United States of America 102, 14344-14349.

Saikali, S., Avril, T., Collet, B., Hamlat, A., Bansard, J. Y., Drenou, B., Guegan, Y., and Quillien, V. (2007). Expression of nine tumour antigens in a series of human glioblastoma multiforme: interest of EGFRvIII, IL-13Ralpha2, gp100 and TRP-2 for immunotherapy. Journal of neuro-oncology 81, 139-148.

Semrau, S., Crosetto, N., Bienko, M., Boni, M., Bernasconi, P., Chiarle, R., and van Oudenaarden, A. (2014). FuseFISF: Robust detection of transcribed fusions in single cells. Cell Reports 6, 18-23.

Schafer, W., Stroh, A., Berghofer, S., Seiler, J., Vey, M., Kruse, M. L., Kern, H. F., Klenk, H. D., and Garten, W. (1995). Two independent targeting signals in the cytoplasmic domain determine trans-Golgi network localization and endosomal trafficking of the proprotein convertase furin. The EMBO journal 14, 2424-2435.

Sottoriva, A., Spiteri, I., Piccirillo, S. G., Touloumis, A., Collins, V. P., Marioni, J. C., Curtis, C., Watts, C., and Tavare, S. (2013). Intratumor heterogeneity in human glioblastoma reflects cancer evolutionary dynamics. Proc Natl Acad Sci USA 110, 4009-4014.

Spigel, D. R., Ervin, T. J., Ramlau, R. A., Daniel, D. B., Goldschmidt, J. H., Jr., Blumenschein, G. R., Jr., Krzakowski, M. J., Robinet, G., Godbert, B., Barlesi, F., et al. (2013). Randomized phase II trial of Onartuzumab in combination with erlotinib in patients with advanced non-small-cell lung cancer. J Clin Oncol 31, 4105-4114.

Surati M, Patel P, Peterson A and Salgia R. (201, 1). Role of MetMAb (OA-5D5) in c-MET active lung malignancies. Expert Opin Biol Ther. 12, 1655-1662

Verhaak, R. G., Hoadley, K. A., Purdom, E., Wang, V., Qi, Y., Wilkerson, M. D., Miller, C. R., Ding, L., Golub, T., Mesirov, J. P., et al. (2010). Integrated genomic analysis identifies clinically relevant subtypes of glioblastoma characterized by abnormalities PDGFRA, IDH1, EGFR, and NFL Cancer cell 17, 98-110.

Viana-Pereira, M., Lopes, J. M., Little, S., Milanezi, F., Basto, D., Pardal, F., Jones, C., and Reis, R. M. (2008). Analysis of EGFR overexpression, EGFR gene amplification and the EGFRvIII mutation in Portuguese high-grade gliomas. Anticancer research 28, 913-920.

Vriend, G. (1990). WHAT IF: a molecular modeling and drug design program. Journal of molecular graphics 8, 52-56, 29.

Weibrecht I, Lundin E, Kiflemariam S, Mignardi M, Grundberg I, Larsson C, Koos B, Nilsson M, and Söderberg O. (2013). In situ detection of individual mRNA molecules and protein complexes or post-translational modifications using padlock probes combined with the in situ proximity ligation assay. Nat Protoc. 8, 355-72.Zhang, Y. W., Su, Y., Lanning, N., Gustafson, M., Shinomiya, N., Zhao, P., Cao, B., Tsarfaty, G., Wang, L. M., Hay, R, and Vande Woude, G. F. (2005). Enhanced growth of human met-expressing xenografts in a new strain of immunocompromised mice transgenic for human hepatocyte growth factor/scatter factor. Oncogene 24, 101-106.

The invention claimed is:

1. A method for detecting a deletion in the MET gene in a human subject, comprising,
    (a) obtaining a nucleic acid sample from the subject, wherein the sample comprises genomic DNA and/or mRNA and
    (b) screening genomic DNA encoding the MET gene using a molecular diagnostic method and detecting the presence of a chromosomal deletion in the MET gene, wherein the deletion consists of loss of part of intron 6, exon 7, and part of exon 8 of the MET gene in the subject and/or
    (c) screening mRNA or cDNA from the MET gene using a molecular diagnostic method and detecting the presence of a deletion which consists of the substantial absence of exons 7 and 8 of the MET mRNA or cDNA.

2. The method of claim 1, wherein the molecular diagnostic method is a nucleic acid detection assay comprising an oligonucleotide, wherein a complex of the oligonucleotide with a template polynucleotide is formed.

3. The method of claim 1, wherein the subject has a condition selected from amyotrophic lateral sclerosis, systemic sclerosis, ulcerative colitis, autism and/or a cancer selected form the group consisting of lymphoma, leukemia, mycosis fungoide, carcinoma, adenocarcinoma, sarcoma, rhabdomyosarcoma, Ewing sarcoma, castration resistant prostate carcinoma, glioma, astrocytoma, blastoma, neuroblastoma, plasmacytoma, histiocytoma, melanoma, adenoma, hypoxic tumor, myeloma, metastatic cancer, bladder cancer, brain cancer, nervous system cancer, squamous cell carcinoma of the head and neck, neuroblastoma, glioblastoma, ovarian cancer, skin cancer, liver cancer, squamous cell carcinomas of the mouth, throat, larynx, and lung, colon cancer, cervical cancer, breast cancer, cervical carcinoma, epithelial cancer, renal cancer, genitourinary cancer, pulmonary cancer, esophageal carcinoma, lung cancer, head and neck carcinoma, hematopoietic cancer, testicular cancer, colorectal cancer, prostatic cancer, and pancreatic cancer.

4. The method according to claim 1, wherein the sample is tissue, a tumor tissue, urine, sperm, saliva, blood, blood plasma, cerebrospinal fluid, blood platelets, and/or exosomes.

* * * * *